US007056935B2

(12) United States Patent
Steiner et al.

(10) Patent No.: US 7,056,935 B2
(45) Date of Patent: *Jun. 6, 2006

(54) ROTAMASE ENZYME ACTIVITY INHIBITORS

(75) Inventors: Joseph P. Steiner, Mount Airy, MD (US); Gregory S. Hamilton, Catonsville, MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 632 days.

This patent is subject to a terminal disclaimer.

(21) Appl. No.: 09/805,249

(22) Filed: Mar. 14, 2001

(65) Prior Publication Data

US 2002/0052410 A1 May 2, 2002

Related U.S. Application Data

(63) Continuation-in-part of application No. 08/551,026, filed on Oct. 31, 1995, now abandoned, which is a continuation-in-part of application No. 09/359,351, filed on Jul. 21, 1999, now Pat. No. 6,509,477, which is a continuation of application No. 08/693,003, filed on Aug. 6, 1996, now abandoned, which is a continuation of application No. 08/479,436, filed on Jun. 7, 1995, now Pat. No. 5,614,547.

(51) Int. Cl.
*A61K 31/40* (2006.01)
*A61K 31/445* (2006.01)
*A61K 38/18* (2006.01)

(52) U.S. Cl. .................. 514/343; 514/317; 514/423; 514/330; 514/422; 514/548

(58) Field of Classification Search ............ 514/354, 514/357, 423, 365, 422, 343, 317, 330, 533; 548/533, 548
See application file for complete search history.

(56) References Cited

U.S. PATENT DOCUMENTS

| | | | |
|---|---|---|---|
| 2,447,587 A | 8/1948 | Martin et al. ............. 260/561 |
| 3,312,554 A | 4/1967 | Wagner et al. ............. 96/114 |
| 3,370,046 A | 2/1968 | Wagner et al. ............. 260/78 |
| 3,396,030 A | 8/1968 | Haas ...................... 96/114 |
| 3,452,182 A | 6/1969 | Haas ...................... 96/35.1 |
| 3,713,834 A | 1/1973 | Fitzgerald ................. 96/114 |
| 3,810,884 A | 5/1974 | Gold ...................... 260/239 |
| 3,833,384 A | 9/1974 | Noonan et al. ............. 96/115 |
| 3,879,205 A | 4/1975 | Fitzgerald et al. .......... 96/114 |
| 3,917,840 A | 11/1975 | Gold ...................... 424/267 |
| 4,105,776 A | 8/1978 | Ondetti et al. ............. 424/274 |
| 4,154,840 A | 5/1979 | Ondetti et al. ............. 424/267 |
| 4,157,418 A | 6/1979 | Heilmann ................. 428/355 |
| 4,172,934 A | 10/1979 | Heilmann ................. 526/298 |
| 4,261,895 A | 4/1981 | Wiskott ................. 260/326.36 |
| 4,374,829 A | 2/1983 | Harris et al. .............. 424/177 |
| 4,401,677 A | 8/1983 | Greenberg et al. .......... 424/317 |
| 4,431,644 A | 2/1984 | Smith et al. .............. 424/246 |
| 4,439,545 A | 3/1984 | Aspisi et al. ............. 521/32 |
| 4,455,366 A | 6/1984 | Hirano et al. ............. 430/381 |
| 4,472,380 A | 9/1984 | Harris et al. ............. 424/177 |
| 4,474,795 A | 10/1984 | Greenberg et al. .......... 424/273 |
| 4,474,799 A | 10/1984 | Greenberg et al. .......... 424/274 |
| 4,633,025 A | 12/1986 | Corey .................... 568/866 |
| 4,650,785 A | 3/1987 | Toyoshima et al. .......... 514/3 |
| 4,668,798 A | 5/1987 | Kim ...................... 548/533 |
| 4,668,822 A | 5/1987 | Corey .................... 562/579 |
| 4,670,584 A | 6/1987 | Toyoshima et al. .......... 562/449 |
| 4,766,110 A | 8/1988 | Ryan et al. ............... 514/19 |
| 4,808,573 A | 2/1989 | Gold et al. ............... 514/19 |
| 4,818,749 A | 4/1989 | Gold et al. ............... 514/19 |
| 4,898,686 A | 2/1990 | Johnson et al. .......... 252/389.2 |
| 5,002,963 A | 3/1991 | De Luca et al. ........... 514/419 |
| 5,128,483 A | 7/1992 | Trybulski et al. .......... 548/531 |
| 5,147,877 A | 9/1992 | Goulet ................... 514/291 |
| 5,192,773 A | 3/1993 | Armistead et al. .......... 514/315 |
| 5,227,467 A | 7/1993 | Durette et al. ............ 530/321 |
| 5,235,066 A | 8/1993 | Askin et al. .............. 548/406 |
| 5,252,579 A | 10/1993 | Skotnicki et al. .......... 514/291 |
| 5,321,009 A | 6/1994 | Baeder et al. ............. 514/4 |
| 5,330,993 A | 7/1994 | Armistead et al. .......... 514/330 |
| 5,385,908 A | 1/1995 | Nelson et al. ............. 514/291 |
| 5,385,918 A | 1/1995 | Connell et al. ............ 514/330 |
| 5,444,042 A | 8/1995 | Bartus et al. ............. 514/2 |
| 5,447,915 A | 9/1995 | Schreiber et al. .......... 514/18 |
| 5,453,437 A | 9/1995 | Schohe et al. ............. 514/424 |
| 5,516,797 A | 5/1996 | Armistead et al. .......... 514/548 |
| 5,527,907 A | 6/1996 | Or et al. ................. 540/456 |
| 5,530,121 A | 6/1996 | Kao et al. ................ 540/456 |
| 5,541,189 A | 7/1996 | Luly et al. ............... 514/291 |
| 5,541,191 A | 7/1996 | Skotnicki et al. .......... 514/291 |
| 5,541,192 A | 7/1996 | Skotnicki et al. .......... 514/291 |

(Continued)

FOREIGN PATENT DOCUMENTS

BE 879158 10/1979

(Continued)

OTHER PUBLICATIONS

Holt et al., "Structure-Activity Studies of Synthetic FKBP Ligands as Peptidyl-prolyl Isomerase Inhibitors", Bioorganic and Medicinal Chemistry Letters, vol. 4, No. 2, pp. 315-320, 1994.

(Continued)

*Primary Examiner*—Vickie Kim
(74) *Attorney, Agent, or Firm*—Foley & Lardner LLP

(57) ABSTRACT

This invention relates to methods of using neurotrophic compounds having an affinity for FKBP-type immunophilins to stimulate or promote neuronal growth or regeneration and to prevent neuronal degeneration.

4 Claims, No Drawings

U.S. PATENT DOCUMENTS

| | | | |
|---|---|---|---|
| 5,543,423 A | 8/1996 | Zelle et al. | 514/332 |
| 5,589,499 A | 12/1996 | Weth | 514/423 |
| 5,599,927 A | 2/1997 | Or et al. | 540/456 |
| 5,604,294 A | 2/1997 | Luly et al. | 540/456 |
| 5,614,547 A | 3/1997 | Hamilton et al. | 514/423 |
| 5,620,971 A | 4/1997 | Armistead et al. | 514/212 |
| 5,621,108 A | 4/1997 | Smith, III et al. | 546/207 |
| 5,696,135 A | 12/1997 | Steiner | 514/317 |
| 5,795,908 A | 8/1998 | Hamilton | 514/423 |
| 5,798,355 A | 8/1998 | Steiner et al. | 514/248 |
| 5,801,197 A | 9/1998 | Steiner | 514/548 |
| 5,843,960 A | 12/1998 | Steiner | 514/317 |
| 5,846,981 A | 12/1998 | Steiner | 514/317 |
| 5,859,031 A | 1/1999 | Hamilton | 514/343 |
| 5,898,029 A | 4/1999 | Lyons et al. | 514/12 |
| 6,037,370 A * | 3/2000 | Armistead | 514/533 |
| 6,124,328 A * | 9/2000 | Armistead | 514/354 |

FOREIGN PATENT DOCUMENTS

| | | |
|---|---|---|
| CA | 1102337 | 6/1981 |
| CA | 1103255 | 6/1981 |
| CA | 1103256 | 6/1981 |
| CA | 1103257 | 6/1981 |
| CA | 5 024 7/91 | 11/1991 |
| CH | 240379 | 12/1945 |
| CN | 86 1 01512 A | 7/1986 |
| DE | 2 320 849 | 11/1973 |
| DE | 2 328 391 | 1/1974 |
| DE | 27 03 828 | 8/1977 |
| DE | 28 45 499 A1 | 3/1979 |
| DE | 35 08 251 A1 | 9/1986 |
| DE | 36 36 278 A1 | 5/1988 |
| DE | 40 15 255 A1 | 11/1991 |
| DE | 44 25 950 A1 | 1/1996 |
| EP | 0 012 401 A1 | 6/1980 |
| EP | 0 038 117 A1 | 10/1981 |
| EP | 0 048 159 A2 | 3/1982 |
| EP | 0 050 800 A1 | 5/1982 |
| EP | 0 088 350 A1 | 9/1983 |
| EP | 0 093 551 A2 | 11/1983 |
| EP | 0 182 523 A | 5/1986 |
| EP | 0 187 547 A2 | 7/1986 |
| EP | 0 196 841 A1 | 10/1986 |
| EP | 0 198 348 A2 | 10/1986 |
| EP | 0 198 352 A2 | 10/1986 |
| EP | 0 309 766 A2 | 4/1989 |
| EP | 0 378 318 A1 | 7/1990 |
| EP | 0 405 994 A2 | 1/1991 |
| EP | 0 564 924 A2 | 10/1993 |
| FR | 1533817 | 7/1968 |
| FR | 2 010 601 A | 2/1970 |
| FR | 2 407 204 | 10/1978 |
| GB | 2 167 075 A | 5/1986 |
| GB | 2 247 456 A | 3/1992 |
| JP | 57-16809 | 1/1982 |
| JP | 63-200060 | 8/1988 |
| WO | WO 88/09789 | 12/1988 |
| WO | WO 91/13088 | 9/1991 |
| WO | WO 92/00278 | 1/1992 |
| WO | WO 92/04370 | 3/1992 |
| WO | WO 92/18478 | 10/1992 |
| WO | WO 92/19593 | 11/1992 |
| WO | WO 92/19745 | 11/1992 |
| WO | WO 92/21313 | 12/1992 |
| WO | WO 93/07269 | 4/1993 |
| WO | WO 93/23548 | 11/1993 |
| WO | WO 93/25546 | 12/1993 |
| WO | WO 94/07858 | 4/1994 |
| WO | WO 95/26337 | 10/1995 |
| WO | WO 96/06097 | 2/1996 |

OTHER PUBLICATIONS

Yamashita et al., "Design, Synthesis and Evaluation of Dual Domain FKBP Lignads", Bioorganic & Medicinal Chemistry Letters, vol. 4, No. 2, pp. 325-328, 1994.

Yamamoto et al., "Stimulation of Hair Growth by Topical Application of FK506, a Potent Immunosuppressive Agent", Journal of Investigative Dermatology, vol. 102, No. 2, pp. 160-164, 1994.

Wang et al., "Synthesis and FKBP Binding of Small Molecule Mimics of the Tricarbonyl Region on FK506", Bioorganic & Medicinal Chemistry Letters, vol. 4, No. 9, pp. 1161-1166, 1994.

Steffan et al., "Base Catalyzed Degradations of Rapamycin", Tetrahedron Letters, vol. 34, No. 23, pp. 3699-3702, 1993.

Steiner et al., "High Brain Densities of the Immunophilin FKBP Colocalized with Calcineurin", Nature, vol. 358, pp. 584-586, 1992.

Stocks et al., "Marcrocyclic Ring Closures Employing the Intramolecular Heck Reaction", Tetrahedron Letters, vol. 36, No. 36, pp. 6555-6558, 1995.

Stocks et al., "The Contribution to Binding of the Pyranoside Substituents in the Excised Binding Domain of FK-506,", Bioorganic & Medicinal Chemistry Letters, vol. 4, No. 12, pp. 1457-1460, 1994.

Tanaka et al., "Structure of FK506: A Novel Immunosuppressant Isolated from Streptomyces", J. Am. Chem. Soc., 109, pp. 5031-5033, 1987.

Tatlock et al., "High Affinity FKBP-12 Ligands Derived from (R)-(-)-Carvone. Synthesis and Evaluation of FK506 Pyranose Ring Replacements", Bioorganic & Medicinal Chemistry Letters, vol. 5, No. 21, pp. 2489-2494, 1995.

Teague et al., "The Affinity of the Excised Binding Domain of FK-506 for the Immunophilin FKBP12", Bioorganic & Medicinal Chemistry Letters, vol. 3, No. 10, pp. 1947-1950, 1993.

Teague et al., "Synthesis of FK506-Cyclosporin Hybrid Macrocycles", Bioorganic & Medicinal Chemistry Letters, vol. 5, No. 20, pp. 2341-2346, 1995.

Teague et al., "Synthesis and Study of a Non Macrocyclic FK506 Derivative", Bioorganic & Medicinal Chemistry Letters, vol. 4, No. 13, pp. 1581-1584, 1994.

Tindall, "Immunointervention with Cyclosporin A in Autoimmune Neurological Disorders", Journal of Autoimmunity, vol. 5 (Supp. A), pp. 301-313, 1992.

Tugwell, "Cyclosporin in the Treatment of Rheumatoid Arthritis", Journal of Autoimmunity, vol. 5 (Supp. A), pp. 231, 240, 1992.

Snyder et al., "Immunophilins and the Nervous System", Nature Medicine, vol. 1, No. 1, pp. 32-37, 1995.

Nakatsuka et al., "Total Synthesis of FK506 and an FKBP Probe Reagent, ($C_8$, $C_9$-$^{13}C_2$)-FK506", J. Am. Chem. Soc., vol. 112, No. 14, pp. 5583-5601, 1990.

Nelson et al., "A Novel Ring Contraction of Rapamycin", Tetrahedron Letters, vol. 35, No. 41, pp. 7557-7560, 1994.

Nicolau et al., "Total Synthesis of Rapamycin", J. Am. Chem. Soc., vol. 115, No. 10, pp. 4419-4420, 1993.

Nicolauo et al., "Total Synthesis of Rapamycin", Chem. Eur. J., 1, No. 5, pp. 318-338, 1995.

Pattenden et al., "Facile Synthesis of the "Tricarbonyl" Subunit in the Immunosuppressant Rapamycin", Tetrahedron Letters, vol. 34, No. 16, pp. 2677-2680, 1993.

Rao et al., "Studies Directed Towards the Synthesis of Immunosuppressive Agent FK-506: Synthesis of the Entire Bottom-Half", Tetrahedron Letters, vol. 32, No. 9, pp. 1251-1254, 1991.

Rao et al., "Studies Directed Towards the Synthesis of Rapamycin: Stereoselective Synthesis of C-1 to C-15 Segment", Tetrahedron Letters, vol. 34, No. 44, pp. 7111-7114 (1993).

Rao et al., "Studies Directed Toward the Synthesis Immunosuppressive Agent FK-506: Construction of the Tricarbonyl Moiety", Tetraheron Letters, vol. 31, No. 10, pp. 1439-1442, 1990.

Schreiber, "Chemistry and Biology of the Immunophilins and Their Immunosuppressive Ligands", Science, vol. 251, pp. 283-287, 1991.

Sharkey et al., "Immuophilins Mediate the Neuroprotective Effects of FK506 in Focal Cerebral Ischaemia", Nature, vol. 371, pp. 336-339, 1994 (Chemical Abstract attached—vol. 121, No. 19).

Skotnicki et al., "Ring Expanded Rapamycin Derivatives", Tetrahedron Letters, vol. 35, No. 2, pp. 201-202, 1994.

Skotnicki et al., "Synthesis of Secorapamycin Esters and Amides", Tetrahedron Letters, vol. 35, No. 2, pp. 197-200, 1994.

Smith, III et al., "Total Synthesis of Rapamycin and Demethoxyrapamycin", J. Am. Chem. Soc., vol. 117, No. 19, pp. 5407-5408, 1995.

Jiang et al., "Induction of Anagen in Telogen Mouse Skin by Topical Application of FK506, a Potent Immunosuppressant", Journal of Investigative Dermatology, vol. 104, No. 4, pp. 523-525, 1995.

Jones et al., "A Formal Synthesis of FK-506. Exploration of Some Alternatives to Macrolactamization", *J. Org. Chem.*, vol. 55, No. 9, pp. 2786-2797, 1990.

Jones et al., Chemistry of Tricarbonyl Hemiketals and Application of Evans' Technology to the Total Synthesis of the Immunosuppressant (-)-FK-506, J. Am. Chem. Soc., vol. 112, No. 8, pp. 2998-3017, 1990.

Kelly et al., "Macrolide Compositions for Treatment of Amyotrophic Lateral Sclerosis", Chemical Abstracts, vol. 122, 114965m, p. 659, 1995.

Kino et al., "FK-506, A Novel Immunosuppressant Isolated From a Streptomyces", Journal of Antibiotics, vol. XI, No. 9, pp. 1249-1255, 1987.

Kocienski et al., "A Synthesis of the C(1)-C(15) Segment of Tsukubaenolide (FK 506)", Tetrahedron Letters, vol. 29, No. 35, pp. 4481-4484, 1988.

Linde II et al., "Straightforward Synthesis of 1,2,3-Tricarbonyl Systems", J. Org. Chem., vol. 56, No. 7, pp. 2534-2538, 1991.

Luengo et al., "Efficient Removal of Pipecolinate from Rapamycin and FK506 by Reaction with n-$Bu_4N^+$ $CN^-$", Tetrahderon Letters, vol. 34, No. 29, pp. 4599-4602, 1993.

Luengo et al., "Synthesis and Structure-Activity Relationships of Macrocyclic FKBP Ligands", Bioorganic & Medicinal Chemistry Letters, vol. 4, No. 2, pp. 321-324, 1994.

Luengo et al., "Studies on the Chemistry of Rapamycin: Novel Transformations under Lewis-Acid Catalysis", Tetrahedron Letters, vol. 34, No. 6, pp. 991-994, 1993.

Luengo et al., "Structure-Activity Studies of Rapamycin Analogs: Evidence that the C-7 Methoxy Group is Part of the Effector Domain and Positioned at the FKBP12-FRAP Interface", Chemistry and Biology, vol. 2, No. 7, pp. 471-481, 1995.

Lyons et al., "Neuronal Regeneration Enhances the Expression of the Immunophilin FKBP-12", Journal of Neuroscience, pp. 2985-2994, 1995.

Munegumi et al., "Diastereoselective Catalytic Hydrogenation of $N^\alpha$Pyruvoyl-(S)-prolinamide", Bull. Chem. Soc. Jpn., vol. 63, No. 6, pp. 1832-1834, 1990.

Hayward et al., "An Application of the Suarez Reaction to the Regiospecific and Stereospecific Synthesis of the $C_{28}$-$C_{42}$ Segment of Rapamycin", pp. 3989-3992, 1993.

Holt et al., "Structure-Activity Studies of Nonmacrocyclic Rapamycin Derivatives", Bioorganic & Medicinal Chemistry Letters, vol. 3, No. 10, pp. 1977-1980, 1993.

Holt et al., "Design, Synthesis, and Kinetic Evaluation of High-Affinity FKBP Ligands and the X-ray Crystal Structures of Their Complexes with FKBP12", J. Am. Chem. Soc., vol. 115, No. 22, pp. 9925-9938, 1993.

Horvath et al., "An Application of the Evans-Prasad 1,3-Syn Diol Synthesis to a Stereospecific Synthesis of the $C_{10}$ -$C_{27}$ Segment of Rapamycin", Tetrahedron Letters, vol. 34, No. 25, pp. 3993-3996, 1993.

Iwabuchi et al., "Effects of Immunosuppressive Peptidyl-Prolyl cis-trans Isomerase (PPlase) Inhibitors, Cyclosporin A, FK506, Ascomycin and Rapamycin, on Hair Growth Initiation in Mouse: Immunosuppression is Not Required for New Hair Growth", Journal of Dermatological Science, 9, pp. 64-69, 1995.

Hayward et al., "Total Synthesis of Rapamycin via a Novel Titanium-Mediated Aldol Macrocyclization Reaction", J. Am. Chem. Soc., vol. 115, No. 20, pp. 9345-9346, 1993.

Goulet et al., "Construction of an FK-506 Analog From Rapamycin-Derived Materials", Tetrahedron Letters, vol. 32, No. 36, pp. 4627-4630, 1991.

Goulet et al., "Degradative Studies on the Tricarbonyl Containing Macrolide Rapamycin", Tetrahedron Letters, vol. 31, No. 34, pp. 4845-4848, 1990.

Harding et al., "A Receptor for the Immunosuppressant FK506 is a cis-trans Peptidyl-Prolyl Isomerase", Nature, vol. 341, pp. 758-760, 1989.

Hauske et al., "Design and Synthesis of Novel FKBP Inhibitors", J. Med. Chem. 1992, vol. 35, No. 23, pp. 4284-4296, 1992.

Hauske et al., "Investigation of the Effects of Synthetic, Non-Cytotoxic Immunophilin Inhibitors on MDR", Bioorganic & Medicinal Chemistry Letters, vol. 4, No. 17, pp. 2097-2102, 1994.

Gold et al., "The Immunosuppressant FK506 Increases Functional Recovery and Nerve Regeneration Following Peripheral Nerve Injury", Restorative Neurology and Neuroscience, 6, pp. 287-296, 1994.

Askin et al., "Chemistry of FK-506: Benzilic Acid Rearrangement of the Tricarbonyl System", Tetrahedron Letters, vol. 30, No. 6, pp. 671-674, 1989.

Askin et al., "Efficient Degradation of FK-506 to a Versatile Synthetic Intermediate", J. Org. Chem., vol. 55, No. 20, pp. 5451-5454, 1990.

Baumann et al., "Synthesis and Oxidative Cleavage of the Major Equilibrium Products of Ascomycin and FK 506", Tetrahedron Letters, vol. 36, No. 13, pp. 2231-2234, 1995.

Bycroft et al., "Efficient Asymmetric Synthesis of α-Amino Acids from α-Keto Acids and Ammonia with Conservation of the Chiral Reagent", J.C.S. Chem. Comm., pp. 988-989, 1975.

Birkenshaw et al., "Synthetic FKBP12 Ligands. Design and Synthesis of Pyranose Replacements", Bioorganic & Medicinal Chemistry Letters, vol. 4, No. 21, pp. 2501-2506, 1994.

Boulmedais et al., "Stereochimie de la Reduction Electrochimique d'α-cetoamides Optiquement Actives II. Electroreduction de Benzoylformamides Derives de la S(-)-proline", Bulletin de la Societe Chimique de France, 9, No. 2, pp. 185-191, 1988.

Caffrey et al., "Synthesis and Evaluaiton of Dual Domain Macrocyclic FKBP12 Ligands", Bioorganic & Medicinal Chemistry Letters, vol. 4, No. 21, pp. 2507-2510, 1994.

Cameron et al., "Immunophilin FK506 Binding Protein Associated with Inositol 1,4,5-trisphosphate Receptor Modulates Calcium Flux", Proc. Natl. Acad. Sci., vol. 92, pp. 1784-1788, 1995.

Caufield et al., "Macrocyclic Immunomodulators", Annual Reports in Methanol Chemistry, 25, Chapter 21, pp. 195-204, 1989.

Chakraborty et al., "Design and Synthesis of a Rapamycin-Based High Affinity Binding FKBP12 Ligand", Chemistry & Biology, vol. 2, pp. 157-161, 1995.

Coleman et al., "Degradation and Manipulations of the Immunosuppressant FK506: Preparation of Potential Synthetic Intermediates", Heterocycles, vol. 28, No. 1, pp. 157-161, 1989.

Dawson et al., "The Immunophilins, FK506 Binding Protein and Cyclophilin, are Discretely Localized in the Brain: Relationship to Calcineurin", Neuroscience, vol. 62, No. 2, pp. 569-580, 1994.

Dawson et al., "Immunosuppressant FK506 Enhances Phosphorylation of Nitric Oxide Synthase and Protects Against Glutamate Neurotoxicity", Proc. Natl. Acad. Sci., vol. 90, pp. 9808-9812, 1993.

Dumont et al., "The Immunosuppressive and Toxic Effects of FK-506 are Mechanistically Related: Pharmacology of a Novel Antagonist of FK-506 and Rapamycin", J. Exp. Med., vol. 176, pp. 751-760, 1992.

Egbertson et al., "Synthetic Route to the 'Tricarbonyl' Region of FK-506", J. Org. Chem., 54, pp. 11-12, 1989.

Feutren, "The Optimal Use of Cyclosporin A in Autoimmune Diseases", Journal of Autoimmunity, 5 (Supp. A), pp. 183-195, 1992.

Finberg et al., "Prevention of HIV-1 Infection and Preservation of CD4 Function by the Binding of CDFs to gp120", Science, vol. 249, pp. 287-291, 1990.

Fisher et al., "On the Remarkable Propensity for Carbon-Carbon Bond Cleavage Reactions in the $C_8$-$C_{10}$ Region of FK-506", J. Org. Chem. 56, pp. 2900-2907, 1991.

Fry, "Psoriasis: Immunopathology and Long-Term Treatment with Cyclosporin", Journal of Autoimmunity, 5 (Supp. A), pp. 277-283, 1992.

Farber, "FKBP12-Ligand-Calcineurin Interactions: Analogues of SBL506", J. Am. Chem. Soc., vol. 117, No. 27, pp. 7267-7268, 1995.

Furber et al., "Studies Relating to the Immunosuppressive Activity of FK506", Tetrahedron Letters, vol. 34, No. 8, pp. 1351-1354, 1993.

Armistead et al., "Design, Synthesis and Structure of Non-Marcocyclic Inhibitors of FKBP12, the Major Binding Protein for the Immunosuppressant FK506", Acta Cryst., D51, pp. 522-528, 1995.

Andrus et al., "Structure-Based Design of an Acyclic Ligand That Bridges FKBP12 and Calcineurin", J. Am. Chem. Soc., vol. 115, No. 22, pp. 10420-10421, 1993.

Yohannes et al., "Degradation of Rapamycin: Retrieval of Major Intact Subunits", Tetrahedron Letters, vol. 33, No. 49, pp. 7469-7472, 1992.

Yohannes et al., "Degradation of Rapamycin: Synthesis of a Rapamycin Derived Fragment Containing the Tricarbonyl and Triene Sectors", Tetrahedron Letters, vol. 34, pp. 2075-2078, 1993.

Williams et al., "Synthesis of the α,β-Diketo Amide Segment of the Novel Immunosuppressive FK506", J. Org. Chem., vol. 53, No. 19, pp. 4643-4344, 1988.

Wasserman et al., "Synthesis of the 'Tricarbonyl' Region of FK-506 Through an Amidophosphorane", J. Org. Chem., vol. 54, No. 12, pp. 2785-2786, 1989.

Waldmann, "Amino Acid Esters as Chiral Auxiliaries in Barbier-Type Reactions in Aqueous Solution", Liebigs Ann. Chem., pp. 1317-1322, 1991.

Mashkouskii et al., "1-8[2-Hydroxy-3-tert-butylaminopropoxy)-indole-3-yl (5-acetamido-1-(s)-carboxypentyl)-DL-alanyl]-L-proline dihydrochloride, a new angiotensin-converting enzyme inhibitor with β-adrenoblocking properties," Khim.-Farm. Zh., 1993, 27(10), 16-20. (Russian).

Baader et al., "Inhibition of prolyl 4-hydroxylase by oxalyl amino acid derivatives in vitro, in isolated microsomes and in embryonic chicken tissues," Biochem. J., 300, 525-530, 1994.

Goodfellow et al., "p-Nitrophenyl 3-Diazopyruvate and Diazopyruvamides, a New Family of Photoactivatable Cross-Linking Bioprobes," Biochemistry, vol. 28, No. 15, pp. 6346-6360, 1989.

Soai et al., "Diastereoselective Reduction of Chiral α-Ketoamides Derived from (S)-Proline Esters with Sodium Borohydride: Preparation of Optically Active α-Hydroxy Acids," J. Chem. Soc. Perkin Trans., pp. 769-772, 1985.

Munegumi et al., "Asymmetric Catalytic Hydrogenations of N-Pyruvoyl-(S)-proline Esters," Bull. Chem. Soc. Jpn., 60, pp. 249-253, 1987.

Teichner et al., "Treatment with Cyclosporine A Promotes Axonal Regeneration in Rats Submitted to Transverse Section of the Spinal Cord," J. Hirnforsch., vol. 34, No. 3, pp. 343-349, 1993.

Somers et al., "Synthesis and Analysis of 506BD, a High-Affinity Ligand for the Immunophilin FKBP," J. Am. Chem. Soc., vol. 113, pp. 8045-8056, 1991.

Shiga et al., "Cyclosporin A protects against ischemia-reperfusion injury in the brain," Brain Research, vol. 595, pp. 145-148, 1992.

Ryba et al., "Cyclosporine A Prevents Neurological Deterioration of Patients with SAH—A Preliminary Report," Acta Neurochiru., vol. 112, pp. 25-27, 1991.

Ocain et al., "A Nonimmunosuppressive Triene-Modified Rapamycin Analog Is A Potent Inhibitor of Peptidyl Prolyl Cis-Trans Isomerase," Biochem. Biophys. Res. Comm., vol. 192, No. 3, pp. 1340-1346, 1993.

Williams et al., "Synthesis of the α, β-Diketo Amide Segment of the Novel Immunosuppressive FK506," J. Org. Chem., vol. 53, pp. 4643-4644, 1988.

Lyons et al., "Immunosuppressant FK506 promotes neurite outgrowth in cultures of PC 12 cells and sensory ganglia," Proc. Natl. Acad. Sci. USA, vol. 91, pp. 3191-3195, 1994.

Kitamura et al., "Suppressive effect of FK-506, a novel immunosuppressant, against MPTP-induced dopamine depletion in the striatum of young C57BL/6 mice," J. Neuroimmunology, vol. 50, pp. 221-224, 1994.

Effenberger et al., "Diastereoselective Addition of Benzenesulfenyl Chloride to 1-Acryloylproyline Esters," Chem. Ber., vol. 122, pp. 545-551, 1989.

Häusler et al., "Hydroxycyclodipeptides by Cyclization of Pyrovoyl Amino Acids," Chem. Ber., vol. 107, pp. 2804-2815, 1974.

Šunjič et al., "Asymmetric Hydrogenation of α-Arylpropenoic Acids Catalyzed by Rhodium(I) Complexes of Chiral Ligands Derived from Some Monosaccharides," Gazzetta Chimica Italiana, vol. 119, pp. 229-233 1989.

Snatzke et al., "Attempted Diastereoselective Preparation and Chiroptical Properties of (2S)-1-(3-Mercapto-2-Methyl-1-Oxopropyl)-L-Proline (Captopril) and Some Congeners," Croatica Chemica Acta, vol. 62, No. 2B, pp. 325-337, 1989.

Nishihara et al., "Conformation and Circular Dichroism of Several N-Acyl-L-prolines," Bulletin of the Chemical Society of Japan, vol. 48, No. 2, pp. 553-555, 1975.

Bender et al., "Periodate of α-Keto γ-Lactams, Enol Oxidation and β-Lactam Formation. Mechanism of Periodate Hydroxylation Reactions," The Journal of Organic Chemistry, vol. 43, No. 17, pp. 3354-3362, 1978.

Steglich et al., "Eine rationelle Synthese von N-Trifluoroacetylaminosäuren," Synthesis—International Journal of Methods in Synthetic Organic Chemistry, No. 6, pp. 399-401, Jun. 1976.

Tucker et al., "Resolution of the Nonsteroidal Antiandrogen 4'-Cyano-3-[(4-fluorophenyl)sulfonyl]-2-hydroxy-2-methyl-3'-(trifluoromethyl)-propionanilide and the Determination of the Absolute Configuration of the Active Enantiomer," J. Med. Chem., vol. 31, pp. 885-887, 1988.

Corey, "Asymmetric Bromolactonization Reaction: Synthesis of Optically Active 2-Hydroxy-2-Methylalkanoic Acids From 2-Methylenealkanoic Acids," Tetrahedron Lett., vol. 28, No. 25, pp. 2801-2804, 1987.

Dunkerton et al., "Synthetic Approaches to Bicyclomycin I. Preparation of Monocyclic Intermediates by Retrograde Michael Cleavage of 6-Alkyl-6-Methoxyhexahydro-3H-Thiazolo [3,4-a] Pyrazine-5, 8-Diones," Tetrahedron Lett., vol. 21, pp. 1803-1805, 1980.

Vasella et al., "Synthesis of D- and I.-5-Oxaproline and of a New Captopril Analogue," Helvetica Chimica Acta, vol. 66, Fasc. 4, Nr. 121, pp. 1241-1252, 1983.

Waldmann et al., "Thermal Diels-Alder Reactions with N-(2-Alkenoyl)-(S)-proline Esters as Chiral Dienophiles," Liebigs Ann. Chem., pp. 681-685, 1990.

Effenberger et al., "Diastereoselective Addition of Thiocarboxylic Acids to 1-(Methacryloyl)proline and -proline Derivatives," Chem. Ber., vol. 122, pp. 553-559, 1989.

Waldmann, "Amino Acid Esters as Chiral Auxillaries in Lewis Acid Catalyzed Diels-Alder Reactions," Liebigs Ann. Chem., pp. 671-680, 1990.

Waldmann, "Amino Acid Esters as Chiral Auxiliaries in Barbier-Type Reactions in Aqueous Solution," Liebigs Ann. Chem., pp. 1317-1322, 1991.

US 5,654,332, 08/1997, Armistead (withdrawn)

* cited by examiner

ROTAMASE ENZYME ACTIVITY INHIBITORS

This application is a continuation-in-part of U.S. application Ser. No. 08/551,026, filed Oct. 31, 1995 now abandoned, and of U.S. application Ser. No. 09/359,351, filed Jul. 21, 1999 now U.S. Pat. No. 6,509,477, which is a continuation of U.S. application Ser. No. 08/693,003, filed Aug. 6, 1996 now abandoned, which is a continuation of U.S. application Ser. No. 08/479,436, filed Jun. 7, 1995, now U.S. Pat. No. 5,614,547, which are hereby incorporated by reference in their entirety.

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity, and their use as small molecule neurotrophic drugs.

The term immunophilin refers to a number of proteins that serve as receptors for the principal immunosuppressant drugs, cyclosporin A (CsA), FK506, and rapamycin. Known classes of immunophilins are cyclophilins and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPlase) or rotamase enzyme activity. It has been determined that rotamase activity has a role in the catalyzation of the interconversion of the cis and trans isomer of the substrate proteins of the immunophilin.

Immunophilins were originally discovered and studied in immune tissue. It was initially postulated by those skilled in the art that inhibition of the immunophilin's rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Instead immunosuppression appears to stem from the formation of a complex of immunosuppressant drugs and immunophilins. It has been shown that the immunophilin-drug complexes interact with ternary protein targets as their mode of action. In the case of FKBP-FK506 and cyclophilin-CsA, the drug-immunophilin complexes bind to the enzyme calcineurin, inhibiting T-cell receptor signaling leading to T-cell proliferation. Similarly, the complex of rapamycin and FKBP interacts with the RAFT1/FRAP protein and inhibits signaling from the IL-2 receptor.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release, and neuronal process extension.

FK506 also augments the phosphorylation of growth-associated protein-43 (GAP43). GAP43 is involved in neuronal process extension and its phosphorylation appears to augment this activity. Accordingly, the effects of FK506, rapamycin, and cyclosporin in neuronal process extension have been examined using PC12 cells. PC12 cells are a continuous line of neuronal-like cells which extend neurites when stimulated by nerve growth factor (NGF).

Surprisingly, it has been found that picomolar concentrations of an immunosuppressant such as FK506 or rapamycin stimulate neurite outgrowth in PC12 cells and sensory neurons, namely dorsal root ganglion cells (DRGs). In whole animal experiments, FK506 has been shown to stimulate nerve regeneration following facial nerve injury and results in functional recovery in animals with sciatic nerve lesions.

More particularly, it has been found that drugs with a high affinity for FKBP are potent rotamase inhibitors and exhibit excellent neurotrophic effects. Snyder et al., "Immunophilins and the Nervous System", *Nature Medicine*, Volume 1, No. 1, January 1995, 32–37. These findings suggest the use of immunosuppressants in treating various peripheral neuropathies and in enhancing neuronal regrowth in the central nervous system (CNS). Studies have demonstrated that neurodegenerative disorders such as senile dementia of the Alzheimer's type (Alzheimer's disease, SDAT), Parkinson's disease, and amyotrophic lateral sclerosis (ALS) may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat SDAT patients with exogenous NGF or other neurotrophic proteins such as brain derived growth factor (BDNF), glial derived growth factor, ciliary neurotrophic factor (CNTF), and neurotropin-3 (NT-3) to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

The present invention provides non-immunosuppressive neurotrophic compounds having an affinity for FKBP-type immunophililins that are extremely potent in augmenting neurite outgrowth, for promoting neuronal growth, and for facilitating regeneration in various neuropathological situations where neuronal repair can be facilitated. Such neuropathological situations include peripheral nerve damage by physical injury or disease state such as diabetes, physical damage to the central nervous system (spinal cord and brain), brain damage associated with stroke, and neurological disorders relating to neurodegeneration, including Parkinson's disease, Alzheimer's disease, and amyotrophic lateral sclerosis.

SUMMARY OF THE INVENTION

This invention relates to neurotrophic compounds having an affinity for FKBP-type immunophilins and to methods of using neurotrophic compounds having an affinity for FKBP-type immunophilins.

One embodiment of this invention is neurotrophic compounds of the formula I, detailed below.

Another embodiment of this invention is neurotrophic compounds of the formula II, detailed below.

Another embodiment of this invention is a method of treating a neurological activity in an animal, comprising: administering to an animal an effective amount of a neurotrophic compound having an affinity for FKBP-type immunophilins to stimulate growth of damaged peripheral nerves or to promote neuronal regeneration, wherein the FKBP-type immunophilin exhibits rotamase activity.

Another embodiment of this invention is a method of treating a neurological disorder in an animal, comprising: administering to an animal an effective amount of a neurotrophic compound having an affinity for FKBP-type immunophilins in combination with an effective amount of a neurotrophic factor selected from the group consisting of neurotrophic growth factor, brain derived growth factor, glial derived growth factor, cilial neurotrophic factor, and neurotropin-3, to stimulate growth of damaged peripheral nerves or to promote neuronal regeneration, wherein the FKBP-type immunophilin exhibits rotamase activity.

Another embodiment of this invention is a method of stimulating growth of damaged peripheral nerves, comprising: administering to damaged peripheral nerves an effective amount of a neurotrophic compound having an affinity for FKBP-type immunophilins to stimulate or promote growth of the damaged peripheral nerves, wherein the FKBP-type immunophilins exhibit rotamase activity.

Another embodiment of this invention is a method for promoting neuronal regeneration and growth in animals, comprising: administering to an animal an effective amount of a neurotrophic compound having an affinity for FKBP-type immunophilins to promote neuronal regeneration, wherein the FKBP-type immunophilins exhibit rotamase activity.

Yet another embodiment of this invention is a method for preventing neurodegeneration in an animal, comprising: administering to an animal an effective amount of a neurotrophic compound having an affinity for FKBP-type immunophilins to prevent neurodegeneration, wherein the FKBP-type immunophilins exhibit rotamase activity.

DETAILED DESCRIPTION OF THE INVENTION

The novel neurotrophic compounds of this invention are relatively small molecules in relation to other known compounds, such as rapamycin, FK506, and cyclosporin.

The neurotrophic compounds of this invention have an affinity for the FK506 binding proteins such as FKBP-12. When the neurotrophic compounds of the invention are bound to FKBP, they have been found to inhibit the prolyl-peptidyl cis-trans isomerase activity, or rotamase activity of the binding protein. The compounds of the invention also have been found to stimulate neurite growth, while not exhibiting an immunosuppressive effect. That is, the compounds of the invention are non-immunosuppresive.

The term "non-immunosuppressive" refers to the inability of the compounds of the present invention to suppress the immune system when compared to a control such as FK506 or cyclosporin A. Assays for determining whether a compound is immunosuppressive are well known to those of ordinary skill in the art. Specific non-limiting examples of well known assays include PMA and OKT3 assays wherein mitogens are used to stimulate proliferation of human peripheral blood lymphocytes (PBC). Compounds added to such assay systems are evaluated for their ability to inhibit such proliferation.

In one embodiment, this invention relates to a novel class of neurotrophic compounds represented by the formula I:

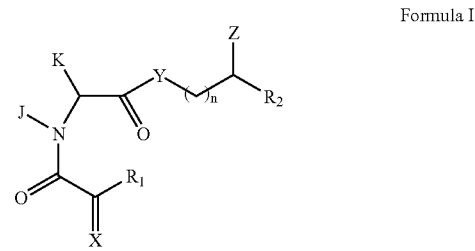

Formula I and pharmaceutically acceptable salts thereof,
wherein Y is $CH_2$, O, NH, or C1–C4 alkyl);
wherein Z and $R_2$ are independently Ar, (C5–C7)-cycloalkyl substituted (C1–C6)-straight or branched alkyl or alkenyl, (C5–C7)-cycloalkenyl substituted (C1–C6)-straight or branched alkyl or alkenyl, or Ar substituted (C1–C6)-straight or branched alkyl or alkenyl, wherein in each case, one or two carbon atoms of the straight or branched alkyl or alkenyl groups may be substituted with 1–2 heteroatoms selected from the group consisting of oxygen, sulfur, SO and $SO_2$ in chemically reasonable substitution patterns, or

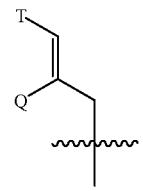

wherein Q is hydrogen, (C1–C6)-straight or branched alkyl or (C1–C6)-straight or branched alkenyl;
wherein T is Ar or substituted 5–7 membered cycloalkyl with substituents at positions 3 and 4 which are independently selected from the group consisting of hydrogen, hydroxyl, O—(C1–C4)-alkyl or O—(C1–C4)-alkenyl and carbonyl;
wherein Ar is selected from the group consisting of monocyclic and bicyclic heterocyclic aromatic ring systems with individual ring sizes being 5 or 6 which may contain in either or both rings a total of 1–4 heteroatoms independently selected from oxygen, nitrogen and sulfur; wherein 1-napthyl, 2-napthyl, 2-furyl, 3-furyl, 2-thienyl, 3-thienyl, 2-pyridyl, 3-pyridyl, 4-pyridyl and phenyl are preferred, and wherein Ar may contain one to three substituents which are independently selected from the group consisting of hydrogen, halo, hydroxyl, hydroxymethyl, nitro, $CF_3$, trifluoromethoxy, (C1–6)-straight or branched alkyl or (C1–C6)-straight or branched alkenyl, O—(C1–C4)-straight or branched alkyl or O—(C1–C4)-straight or branched alkenyl, O-benzyl, O-phenyl, amino, 1,2-methylenedioxy, carbonyl and phenyl;
wherein $R_1$ is either hydrogen or U; X is either oxygen or CH—U, provided that if $R_1$ is hydrogen, then X is CH—U, or if X is oxygen then $R_1$ is U;
wherein U is hydrogen, O—(C1–C4)-straight or branched alkyl or O—(C1–C4)-straight or branched alkenyl, (C1–C6)-straight or branched alkyl or (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C1–C4)-alkyl or (C1–C4)-alkenyl]-Ar or Ar (Ar as described above);

wherein J is hydrogen or C1 or C2 alkyl or benzyl; K is (C1–C4)-straight or branched alkyl, benzyl or cyclohexylethyl; or wherein J and K may be taken together to form a 5–7 membered heterocyclic ring which may contain an oxygen (O), sulfur (S), SO or SO$_2$ substituted therein; and wherein n is 0–3.

The stereochemistry at position 1 (Formula I) is (R) or (S), with (S) preferred. The stereochemistry at position 2 is (R) or (S).

In a second embodiment, a novel class of neurotrophic compounds of this invention are represented by the formula II:

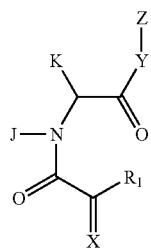

Formula II and pharmaceutically acceptable salts thereof, wherein Y is O, NH, or N—(C1–C4 alkyl);

wherein Z is hydrogen, CHL-Ar, (C1–C6)-straight or branched alkyl, C1–C6)-straight or branched alkenyl, (C5–C7)-cycloalkyl, (C5–C7)-cycloalkenyl or Ar substituted (C1–C6)-alkyl or alkenyl, or

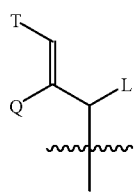

wherein L and Q are independently hydrogen, (C1–C6)-straight or branched alkyl or (C1–C6)-straight or branched alkenyl;

wherein T is Ar or substituted cyclohexyl with substituents at positions 3 and 4 which are independently selected from the group consisting of hydrogen, hydroxyl, O—(C1–C4)-alkyl or O—(C1–C4)-alkenyl and carbonyl;

wherein Ar is selected from the group consisting of 1-napthyl, 2-napthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, CF$_3$, (C1–C6)-straight or branched alkyl or C1–C6)-straight or branched alkenyl, O—(C1–4)-straight or branched alkyl or O—(C1–C4)-straight or branched alkenyl, O-benzyl, O-phenyl, amino and phenyl;

wherein R$_1$ is either hydrogen or U; X is either oxygen or CH—U, provided that if R$_1$ is hydrogen, then X is CH—U, or if X is oxygen then R$_1$ is U;

wherein U is hydrogen, O—(C1–C4)-straight or branched alkyl or O—(C1–C4)-straight or branched alkenyl, C1–C6-straight or branched alkyl, Ar or C1–C6-straight or branched alkenyl, C5–C7-cycloalkyl, (C5–C7)-cycloalkenyl substituted with (C1–C4)-straight or branched alkyl or (C1–C4)-straight or branched alkenyl, 2-indolyl, 3-indolyl, [(C1–C4)-alkyl or (C1–C4)-alkenyl]-Ar or Ar (Ar as described above);

wherein J is hydrogen or C1 or C2 alkyl or benzyl; K is (C1–C4)-straight or branched alkyl, benzyl or cyclohexylethyl; or wherein J and K may be taken together to form a 5–7 membered heterocyclic ring which may contain an oxygen (O), sulfur (S), SO or SO$_2$ substituted therein.

The stereochemistry at position 1 (Formula II) is (R) or (S), with (S) preferred.

The compounds of this invention exist as stereoisomeric forms, either as enantiomers or diastereoisomers. The stereochemistry at position 1 of Formula I or II is R or S, with S preferred. Included within the scope of the invention are the enantiomers, the racemic form, and the diastereoisomeric mixtures. Enantiomers as well as diastereoisomers can be separated by methods known to those skilled in the art.

It is known that immunophilins such as FKBP preferentially recognize peptide substrates containing Xaa-Pro-Yaa motifs, where Xaa and Yaa are lipophilic amino acid residues. Schreiber et al. 1990 *J. Org. Chem.* 55, 4984–4986; Harrison and Stein, 1990 *Biochemistry*, 29, 3813–3816. Thus, modified prolyl peptidomimetic compounds bearing lipophilic substituents should bind with high affinity to the hydrophobic core of the FKBP active site and inhibit its rotamase activity.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; aralkyl halides like benzyl and phenethyl bromides; and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to animals, including mammals other than humans, for treatment of various neurological disorders.

The novel compounds of the present invention are potent inhibitors of rotamase activity and possess an excellent degree of neurotrophic activity. The neurotrophic activity is useful in the stimulation of growth of damaged neurons, the promotion of neuronal regeneration, the prevention of neurodegeneration, and in the treatment of several neurological disorders known to be associated with neuronal degeneration and peripheral neuropathies. The neurological disorders that may be treated include, but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, porphyria, or Guillain-Barré syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal and intracranial injection or infusion techniques.

To be effective therapeutically, the compounds of the invention should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, as do olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

METHODS AND PROCEDURES $K_i$ Test Procedure

Inhibition of the peptidyl-prolyl isomerase (rotamase) activity of the inventive compounds can be evaluated by known methods described in the literature (Harding, M. W. et al. *Nature* 341: 758–760 (1989); Holt et al. *J. Am. Chem. Soc.* 115: 9923–9938). These values are obtained as apparent $K_i$ values and are presented in Table I. The cis-trans isomerization of an phenylalanine-proline bond in a model substrate, N-succinyl-Ala-Phe-Pro-Phe-p-nitroanilide (SEQ ID NO: 1), is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 µL of ice cold assay buffer (25 mM HEPES, pH 7.8, 100 mM NaCl), 10 µL of FKBP (2.5 µM in 10 mM Tris-Cl pH 7.5, 100 mM NaCl, 1 mM dithiothreitol), 25 µL of chymotrypsin (50 mg/ml in 1 mM HCl) and 10 µL of test compound at various concentrations in dimethyl sulfoxide. The reaction is initiated by the addition of 5 µL of substrate (succinyl-Ala-Phe-Pro-Phe-para-nitroanilide (SEQ ID NO: 1), 5 mg/mL in 2.35 mM LiCl in trifluoroethanol).

The absorbance at 390 nm versus time is monitored for 90 sec using a spectrophotometer and the rate constants are determined from the absorbance versus time data files.

The data for these experiments are presented in Table I and in Table II.

TABLE I

| No. | Z | $R_1$ | m | $K_i$ µM |
|---|---|---|---|---|
| 1 | Benzyl | Phenyl | 2 | 1.5 |
| 2 | 3-Phenylpropyl | Phenyl | 2 | — |
| 3 | 4-(4-Methoxyphenyl)butyl | Phenyl | 2 | — |
| 4 | 4-Phenylbutyl | Phenyl | 2 | 0.35 |
| 5 | Phenethyl | Phenyl | 2 | 1.1 |
| 6 | 4-Cyclohexylbutyl | Phenyl | 2 | 0.4 |
| 7 | Benzyl | Methoxy | 2 | 80 |
| 8 | 4-Cyclohexylbutyl | Methoxy | 2 | 6 |
| 9 | 3-Cyclohexylpropyl | Methoxy | 2 | 20 |
| 10 | 3-Cyclopentylpropyl | Methoxy | 2 | 35 |
| 11 | Benzyl | 2-Furyl | 2 | 3 |
| 12 | 4-Cyclohexylbutyl | 3,4,5-Trimethoxyphenyl | 2 | 0.04 |
| 13 | 3-Phenoxybenzyl | 3,4,5-Trimethoxyphenyl | 2 | 0.018 |
| 14 | 4-Phenylbutyl | 3,4,5-Trimethoxyphenyl | 2 | 0.019 |
| 15 | 3-(3-Indolyl)propyl | 3,4,5-Trimethoxyphenyl | 2 | 0.017 |
| 16 | 4-(4-Methoxyphenyl)butyl | 3,4,5-Trimethoxyphenyl | 2 | 0.013 |
| 17 | 3-phenyl-1-propyl | 1,1-dimethylpropyl | 1 | 0.042 |
| 18 | 3-phenyl-1-prop-2-(E)-enyl | 1,1-dimethylpropyl | 1 | 0.125 |
| 19 | 3-(3,4,5-trimethoxyphenyl)-1-propyl | 1,1-dimethylpropyl | 1 | 0.025 |
| 20 | 3-(3,4,5-trimethoxyphenyl)-1-prop-2-(E)-enyl | 1,1-dimethylpropyl | 1 | 0.125 |
| 21 | 3-(4,5-dichlorophenyl)-1-prop-2-(E)-enyl | 1,1-dimethylpropyl | 1 | 2.50 |
| 22 | 3-(2,5-dimethoxyphenyl)-1-prop--2-(E)-enyl | 1,1-dimethylpropyl | 1 | 0.450 |
| 23 | 3-(3-pyridyl)-1-propyl | 1,1-dimethylpropyl | 1 | 0.0075 |
| 24 | 3-phenyl-1-propyl | cyclohexyl | 1 | 0.082 |

TABLE II

| No. | m | n | Z | $R_2$ | $R_1$ | $K_i$ nM |
|---|---|---|---|---|---|---|
| 25 | 2 | 0 | 3-Phenylpropyl | 3-(3-Pyridyl)propyl | Phenyl | 56 |
| 26 | 2 | 0 | 3-Phenylpropyl | 3-(2-Pyridyl)propyl | Phenyl | 50 |
| 27 | 2 | 0 | 3-Phenylpropyl | 2-(4-Methoxyphenyl)ethyl | Phenyl | 270 |
| 28 | 2 | 0 | 3-Phenylpropyl | 3-Phenylpropyl | Phenyl | — |

TABLE II-continued

| No. | m | n | Z | $R_2$ | $R_1$ | $K_i$ nM |
|---|---|---|---|---|---|---|
| 29 | 2 | 0 | 3-Phenylpropyl | 3-Phenylpropyl | 3,4,5-Trimethoxyphenyl | 1.0 |
| 30 | 2 | 0 | 3-Phenylpropyl | 2-(3-Pyridyl) | 3,4,5-Trimethoxyphenyl | 3.0 |
| 31 | 2 | 0 | 3-Phenylpropyl | 3-(2-Pyridyl) | 3,4,5-Trimethoxyphenyl | 1.0 |
| 32 | 2 | 0 | 3-Phenylpropyl | 3-(4-Methoxyphenyl)propyl | 3,4,5-Trimethoxyphenyl | 3.0 |
| 33 | 2 | 0 | 3-Phenylpropyl | 3-(3-Pyridyl)propyl | 3-Iso-propoxyphenyl | 2.0 |
| 34 | 1 | 1 | 3-pyridyl | 3-phenyl | 1,1-dimethylpropyl | 0.019 |

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% $CO_2$. Twenty-four hours later, the DRGs were treated with various concentrations of nerve growth factor (NGF), immunophilin ligands or combinations of NGF plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs were cultured per well, and each treatment was performed in duplicate.

The data for the drug alone (e.g., immunophilin ligand) experiments are presented in Table III.

TABLE III

Neurite Outgrowth in Chick DRG

| Compound | $ED_{50}$, nM Neurite Outgrowth in DRG Cultures |
|---|---|
| 1 | 25–100 |
| 2 | 10–20 |
| 3 | 0.500 |
| 4 | 25–100 |
| 5 | 25–100 |
| 6 | 10–20 |
| 7 | >10,000 |
| 8 | >10,000 |
| 9 | >10,000 |
| 10 | >10,000 |
| 11 | 1000 |
| 12 | 0.031 |
| 13 | 0.180 |
| 14 | 1–5 |
| 15 | 0.055 |

TABLE III-continued

Neurite Outgrowth in Chick DRG

| Compound | $ED_{50}$, nM Neurite Outgrowth in DRG Cultures |
|---|---|
| 16 | 0.030 |
| 17 | 0.053 |
| 18 | 105 |
| 19 | 80 |
| 20 | 190 |
| 21 | 85 |
| 22 | 0.8 |
| 23 | 0.05 |
| 24 | 0.13 |
| 25 | 1–5 |
| 26 | 0.063 |
| 27 | 10–20 |
| 28 | 0.0044 |
| 29 | 0.61 |
| 30 | 0.95 |
| 31 | 25 |
| 32 | 0.50 |
| 33 | 0.30 |
| 34 | 0.07 |

EXAMPLES

The inventive compounds may be prepared by a variety of synthetic sequences that utilize established chemical transformations. The general pathway to the present compounds is described in Scheme 1. N-glyoxylproline derivatives may be prepared by reacting L-proline methyl ester with methyl oxalyl chloride as shown in Scheme I. The resulting oxamates may be reacted with a variety of carbon nucleophiles to obtain intermediates compounds. These intermediates are then reacted with a variety of alcohols, amides, or protected amino acid residues to obtain the propyl esters, ketones, acids, and amides of the invention.

Scheme I

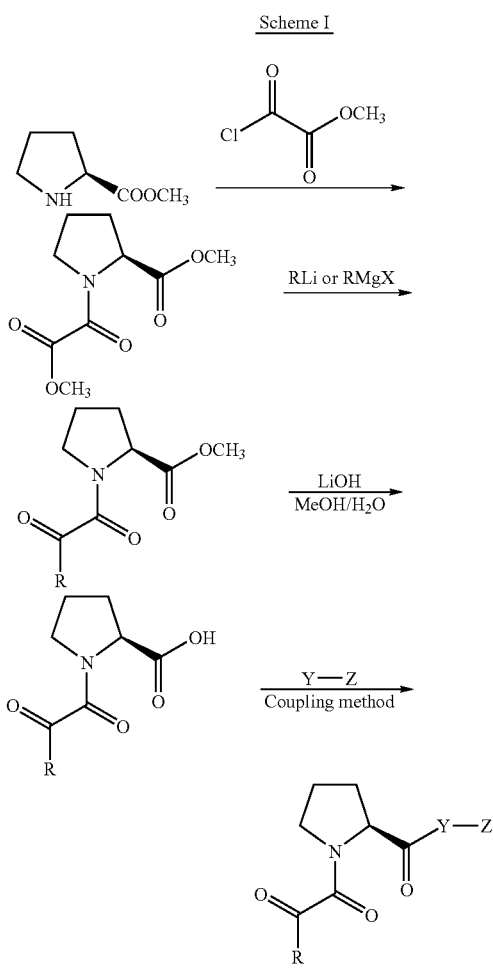

Example 1

Synthesis of methyl (2S)-1-(1,2-dioxo-2-methoxyethyl)-2-pyrrolidinecarboxylate.

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Example 2

General procedure for the synthesis of pyrrolidinyl alkyl oxamates. Exemplified for methyl (2S)-1-(1,2-dioxo-3,3-dimethylpentyl)-2-pyrrolidinecarboxylate.

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.oM solution of 1,1-dimethylpropylmagnesium chloridein THF. After stirring the resulting homogenous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl$_3$): d 0.88 (t, 3H); 1.22,1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J—8.4, 3.4).

Example 3

General procedure for the preparation of pyrrolidine carboxylic acids. Exemplified for (2S)-1-(1,2-dioxo-3,3-dimethylpentyl)-2-pyrrolidinecarboxylic acid.

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 min and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl$_3$): δ 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

Example 4

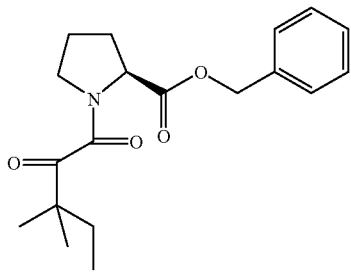

Benzyl (2S)-1-(3,3-dimethyl-1,2-dioxopentyl)-2-pyrrolidinecarboxylate.

A mixture of (2S)-1-(1,2-dioxo-3,3-dimethylpentyl)-2-pyrrolidine-carboxylic acid (500 mg; 2.07 mmol), benzyl alcohol (335 mg; 3.10 mmol), dicyclohexylcarbodiimide (683 mg; 3.31 mmol), 4-dimethylaminopyridine (84 mg; 0.69 mmol) and camphorsulphonic acid (160 mg; 0.69 mmol) in methylene chloride (30 mL) was stirred overnight under a nitrogen atmosphere. The reaction mixture was filtered through Celite to remove solids and concentrated in vacuo, and the crude material was purified on a flash column (25% ethyl acetate in hexane) to obtain 680 mg of the product as a colorless oil. $^1$H NMR (CDCl$_3$; 300 MHz) δ 0.85 (t, 3H); 1.19 (s, 3H); 1.22 (s, 3H); 1.61–2.25 (m, 6H); 3.46–3.56 (m, 2H); 4.58 (dm, 1H); 5.18 (d, 2H, 7.35 (br, 5H).

Example 5

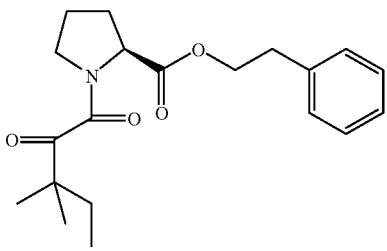

2-Phenyl-1-ethyl (2S)-1-(3,3-dimethyl-1,2-dioxopentyl)-2-pyrrolidinecarboxylate.

A mixture of (2S)-1-(1,2-dioxo-3,3-dimethylpentyl)-2-pyrrolidine-carboxylic acid (570 mg; 2.36 mmol), phenethyl alcohol (432 mg; 3.54 mmol), dicyclohexylcarbodiimide (780 mg; 3.78 mmol), 4-dimethylaminopyridine (98 mg; 0.79 mmol) and camphorsulphonic acid (183 mg; 0.79 mmol) in methylene chloride (30 mL) was stirred overnight under a nitrogen atmosphere. The reaction mixture was filtered through Celite to remove solids and concentrated in vacuo, and the crude material was purified on a flash column (25% ethyl acetate in hexane) to obtain 600 mg of the product as a colorless oil. $^1$H NMR (CDCl$_3$; 300 MHz) δ0.87 (t, 3H); 1.21 (s, 3H); 1.25 (s, 3H); 1.64–1.94 (m, 6H); 2.17 (m, 1H); 2.97 (m, 2H); 3.49 (m, 2H); 4.36 (m, 2H); 4.51 (m, 1H); 7.22–7.33 (m, 5H).

Example 6

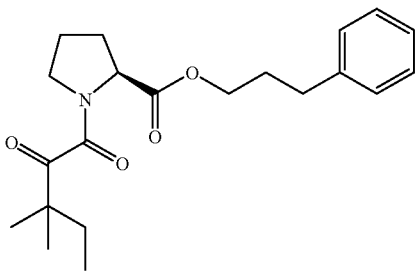

General procedure for the synthesis of prolyl esters. Exemplified for 3-phenyl-1-propyl (2S)-1-(3,3-dimethyl-1,2-dioxopentyl)-2-pyrrolidinecarboxylate. A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulphonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of Example 1 as a colorless oil. $^1$H NMR (CDCl$_3$; 300 MHz): δ 0.84 (t, 3H); 1.19 (s, 3H); 1.23 (s, 3H); 1.70 (dm, 2H); 1.98 (m, 5H); 2.22 (m, 1H); 2.64 (m, 2H); 3.47 (m, 2H); 4.14 (m, 2H); 4.51 (d, 1H); 7.16 (m, 3H); 7.26 (m, 2H). Example 6 is compound 17 in Tables I and III.

Example 7

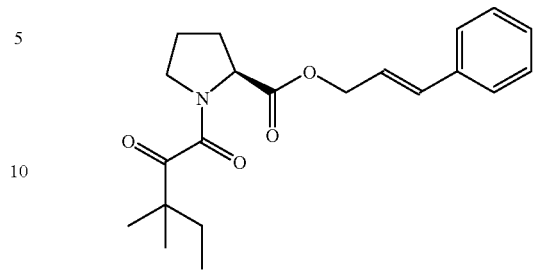

3-phenyl-1-prop-2-(E)-enyl (2S)-1-(3,3-dimethyl-1,2-dioxopentyl)-2-pyrrolidinecarboxylate, 80%, $^1$H NMR (CDCl$_3$; 360 Mhz): δ 0.86 (t, 3H); 1.21 (s, 3H); 1.25 (s, 3H); 1.54–2.10 (m, 5H); 2.10–2.37 (m, 1H); 3.52–3.55 (m, 2H); 4.56 (dd, 1H, J=3.8, 8.9); 4.78–4.83 (m, 2H); 6.27 (m, 1H); 6.67 (dd, 1H, J=15.9); 7.13–7.50 (m, 5H). This compound was prepared by the method of Example 3 from (2S)-1-(1,2-dioxo-3,3-dimethylpentyl)-2-pyrrolidine-carboxylic acid. Example 7 is compound 18 in Tables I and III.

Example 8

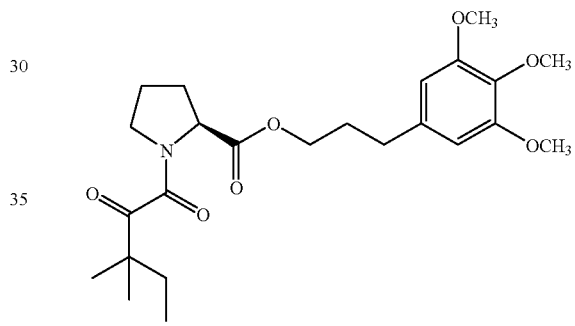

3-(3,4,5-trimethoxyphenyl)-1-propyl (2S)-1-(3,3-dimethyl-1,2-dioxopentyl)-2-pyrrolidine-carboxylate, 61%, $^1$H NMR (CDCl$_3$; 300 MHz): δ 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H). This compound was prepared by the method of Example 3 from (2S)-1-(1,2-dioxo-3,3-dimethylpentyl)-2-pyrrolidine-carboxylic acid. Example 8 is compound 19 in Tables I and III.

Example 9

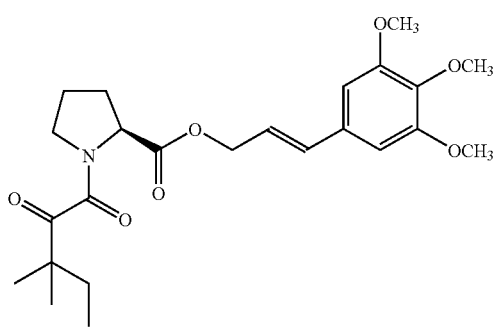

3-(3,4,5-trimethoxyphenyl)-1-prop-2-(E)-enyl (2S)-1-(3,3-dimethyl-1,2-dioxopentyl)-2-pyrrolidine carboxylate, 66%, ¹H NMR (CDCl₃; 360 MHz): δ 0.85 (t, 3H); 1.22 (s, 3H); 1.25 (s, 3H); 1.50–2.11 (m, 5H); 2.11–2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (s, 2H). This compound was prepared by the method of Example 3 from (2S)-1-(1,2-dioxo-3,3-dimethylpentyl)-2-pyrrolidine-carboxylic acid. Example 9 is compound 20 in Tables I and III.

Example 10

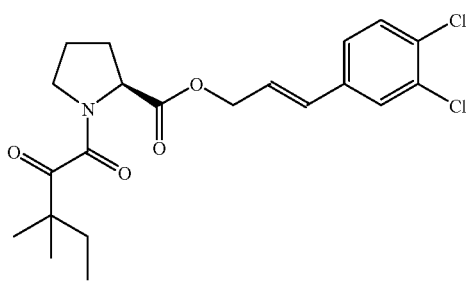

3-(4,5-Dichlorophenyl)-1-prop-2-(E)-enyl (2S)-1-(3,3-dimethyl-1,2-dioxopentyl)-2-pyrrolidine carboxylate, 70%, ¹H NMR (CDCl₃; 360 MHz): δ 0.85 (t, 3H); 1.21 (s, 3H); 1.25 (s, 3H); 1.51–1.87 (m, 2H); 1.87–2.39 (m, 4H); 3.51–3.57 (m, 2H); 4.50–4.61 (dd, 1H, J—3.4, 8.6); 4.80 (d, 2H, J=6.0); 6.20–6.34 (m, 1H); 6.50–6.66 (d, 1H, J=16); 7.13–7.24 (dd, 1H, J=1.8, 8.3); 7.39 (d, 1H, J=8.3); 7.47 (s, 1H). This compound was prepared by the method of Example 3 from (2S)-1-(1,2-dioxo-3,3-dimethylpentyl)-2-pyrrolidine-carboxylic acid. Example 10 is compound 21 in Tables I and III.

Example 11

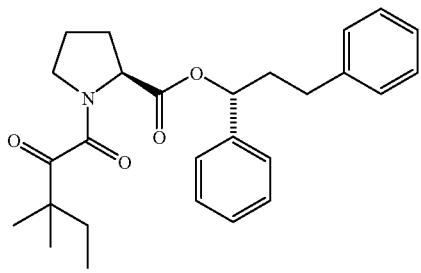

(1R)-1,3-Diphenyl-1-propyl (2S)-1-(3,3-dimethyl-1,2-dioxopentyl)-2-pyrrolidinecarboxylate, 90%, ¹H NMR (CDCl₃; 360 MHz): δ 0.85 (t, 3H); 1.20 (s, 3H); 1.23 (s, 3H); 1.49–2.39 (m, 7H); 2.46–2.86 (m, 2H); 3.25–3.80 (m, 2H); 4.42–4.82 (m, 1H); 5.82 (td, 1H, J=1.8, 6.7); 7.05–7.21 (m, 3H); 7.21–7.46 (m, 7H). This compound was prepared by the method of Example 3 from (2S)-1-(1,2-dioxo-3,3-dimethylpentyl)-2-pyrrolidine-carboxylic acid.

Example 12

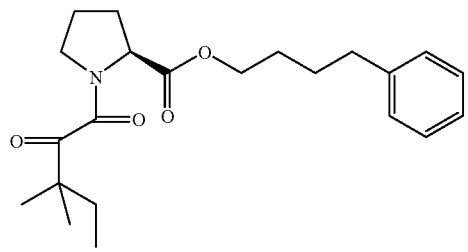

4-Phenyl-1-butyl (2S)-1-(3,3-dimethyl-1,2-dioxopentyl)-2-pyrrolidinecarboxylate.

¹H NMR (CDCl₃; 300 MHz): δ 0.84 (t, 3H); 1.22 (s, 3H); 1.25 (s, 3H); 1.64–2.01 (m, 9H); 2.23 (m, 1H); 2.64 (m, 2H); 3.48–3.53 (m, 2H); 4.17 (m, 2H); 4.52 (m, 1H); 7.18 (m, 3H); 7.27 (m, 2H).

Example 13

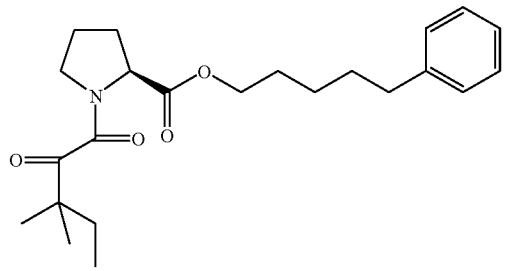

5-Phenyl-1-pentyl (2S)-1-(3,3-dimethyl-1,2-dioxopentyl)-2-pyrrolidinecarboxylate.

¹H NMR (CDCl₃; 300 MHz): δ 0.87 (t, 3H); 1.22 (s, 3H); 1.25 (s, 3H); 1.39 (m, 2H); 1.63–1.99 (m, 9H); 2.22 (m, 1H); 2.64 (m, 2H); 3.46–3.54 (m, 2H); 4.14 (m, 2H); 4.50 (m, 1H); 7.16 (m, 3H); 7.26 (m, 2H).

Examples 12 and 13 were prepared according to the synthetic procedure outlined for Examples 1–3, except that the requisite phenyl alcohols in the reaction mixture were 4-phenylbutan-1-ol and 5-phenylpentan-1-ol, respectively.

Example 14

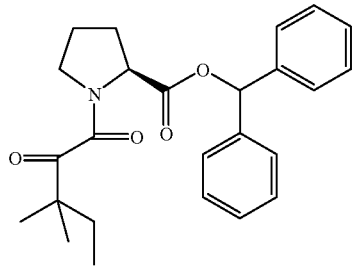

1,1-Diphenylmethyl (2S)-1-(3,3-dimethyl-1,2-dioxopentyl)-2-pyrrolidinecarboxylate.

¹H NMR (CDCl₃; 300 MHz): δ 0.84 (t, 3H); 1.17 (s, 3H); 1.19 (s, 3H); 1.54–2.25 (m, 6H); 3.50 (m, 2H); 4.67 (m, 1H); 5.86 (s, 1H); 7.28–7.39 (m, 10H).

Example 15

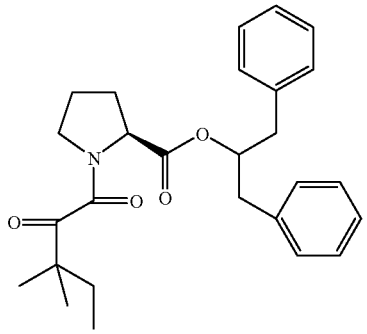

1,3-diphenyl-2-propyl (2S)-1-(3,3-dimethyl-1,2-dioxopentyl)-2-pyrrolidinecarboxylate.

$^1$H NMR (CDCl$_3$; 300 MHz): δ 0.87 (t, 3H); 1.20 (s, 3H); 1.24 (s, 3H); 1.25–2.02 (m, 6H); 2.74, 2.84 (m, 4H total); 3.53 (m, 2H); 4.04 (m, 1H); 4.42 (m, 1H); 7.22 (m, 6H); 7.30 (m, 4H).

Example 16

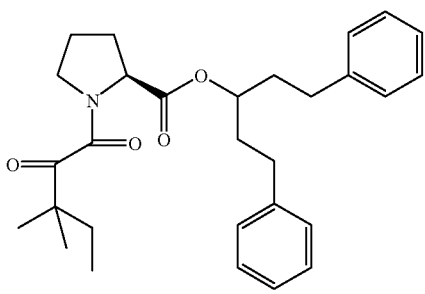

1,5-diphenyl-3-pentyl (2S)-1-(3,3-dimethyl-1,2-dioxopentyl)-2-pyrrolidinecarboxylate.

$^1$H NMR (CDCl$_3$; 300 MHz): δ 0.87 (t, 3H); 1.23 (s, 3H); 1.27 (s, 3H); 1.61–2.06 (m, 9H); (m, 2H); 2.28 (m, 1H); 2.57–2.74 (m, 4H); 3.52–3.56 (m, 2H); 4.49–4.59 (m, 1H); 5.02 (m, 1H); 7.14–7.30 (m, 10H).

Example 17

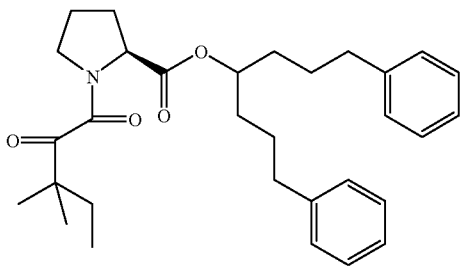

1,7-diphenyl-4-heptyl (2S)-1-(3,3-dimethyl-1,2-dioxopentyl)-2-pyrrolidinecarboxylate.

$^1$H NMR (CDCl$_3$; 300 mHZ): δ 0.86 (t, 3H); 1.23 (s, 3H); 1.25 (s, 3H); 1.44–1.98 (m, 13H); 2.21 (m, 1H); 2.59 (m, 4H); 3.45–3.63 (m, 2H); 4.48–4.52 (dd, 1H, J=2.7, 6.5); 4.99 (m, 1H); 7.08–7.18 (m, 6H); 7.21–7.29 (m, 4H).

Examples 14–17 were prepared according to the synthetic procedure outlined for Examples 1–3, except that the requisite diphenyl alcohols in the reaction mixture were 1,1-diphenylmethanol, 1,3-diphenylpropan-2-ol, 1,5-diphenylpentan-3-ol, and 1,7-diphenylheptan-4-ol, respectively.

Example 18

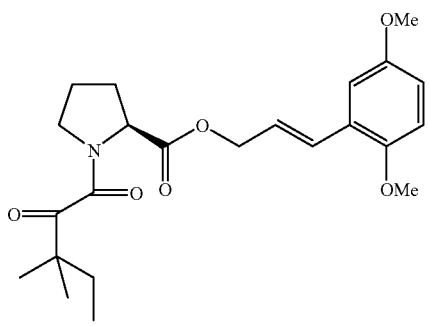

3-(2,5-Dimethoxyphenyl)-1-prop-2(E)-enyl (2S)-1-(3,3-dimethyl-1,2-dioxopentyl)-2-pyrrolidinecarboxylate.

$^1$H NMR (CDCl$_3$; 300 MHz): δ 0.87 (t, 3H); 1.22 (s, 3H); 1.26 (s, 3H); 1.67 (m, 2H); 1.78 (m, 1H); 2.07 (m, 2H); 2.26 (m, 1H); 3.52 (m, 2H); 3.78 (s, 3H); 3.80 (s, 3H); 4.54 (m, 1H); 4.81 (m, 2H); 6.29 (dt, 1H, J=15.9); 6.80 (s, 2H); 6.95 (d, 1H, J=15.9); 6.98 (s, 1H). Example 18 is compound 22 in Tables I and III.

Example 19

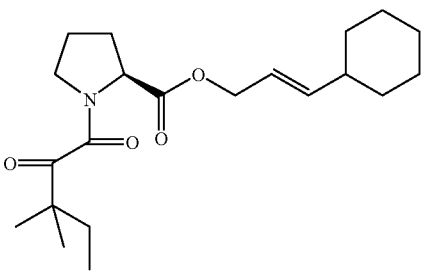

3-Cyclohexyl-1-prop-2(E)-enyl (2S)-1-(3,3-dimethyl-1,2-dioxopentyl)-2-pyrrolidinecarboxylate.

$^1$H NMR (CDCl$_3$; 360 MHz): δ 0.86 (t, 3H); 1.13–1.40 (m+2 singlets, 9H total); 1.50–1.87 (m, 8H); 1.87–2.44 (m, 6H); 3.34–3.82 (m, 2H), 4.40–4.76 (m, 3H); 5.35–5.60 (m, 1H); 5.60–5.82 (dd, 1H, J=6.5, 16).

Examples 18 and 19 were prepared according to the synthetic procedure outlined for Examples 1–3, except that the requisite trans-allylic alcohols in the reaction mixture were 3-(2,5-Dichlorophenyl)-1-prop-2(E)-enol and 3-Cyclohexyl-1-prop-2(E)-enol, respectively.

Example 20

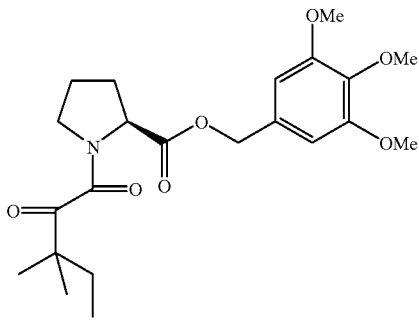

(3,4,5-Trimethoxy)benzyl (2S)-1-(3,3-dimethyl-1,2-dioxopentyl)-2-pyrrolidinecarboxylate.

¹H NMR (CDCl₃; 300 MHz): δ 0.85 (t, 3H); 1.20 (s, 3H); 1.22 (s, 3H); 1.58–1.81 (m, 2H); 1.82–2.27 (m, 4H); 3.52 (m, 2H); 3.84 *s, 3H); 3.87 (s, 6H); 4.55 (m, 1H); 5.13 (s, 2H); 6.59 (s, 2H).

Example 21

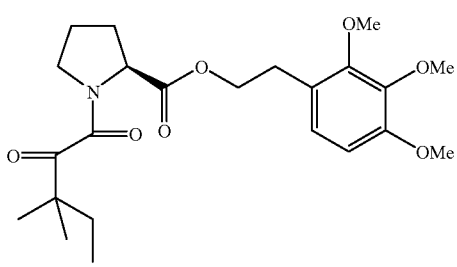

2-(3,4,5-Trimethoxyphenyl)-1-ethyl (2S)-1-(3,3-dimethyl-1,2-dioxopentyl)-2-pyrrolidinecarboxylate ¹H NMR (CDCl₃; 300 MHz): δ 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H).

Example 22

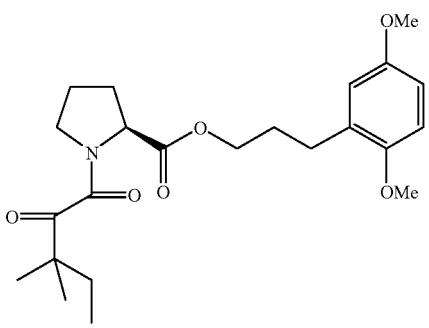

3-(2,5-Dimethoxyphenyl)-1-propyl (2S)-1-(3,3-dimethyl-1,2-dioxopentyl)-2-pyrrolidinecarboxylate.

¹H NMR (CDCl₃; 300 MHz): δ 0.87 (t, 3H); 1.22 (s, 3H); 1.26 (s, 3H); 1.69 (m, 2H); 1.96 (m, 5H); 2.24 (m, 1H); 2.68 (m, 2H); 3.55 (m, 2H); 3.75 (s, 3H); 3.77 (s, 3H); 4.17 (m, 2H); 4.53 (d, 1H); 6.72 (m, 3H).

Examples 20, 21, and 22 were prepared according to the synthetic procedure outlined for Examples 1–3, except that the requisite di- or trimethoxyphenyl-substituted alcohols in the reaction mixture were (3,4,5-Trimethoxy)benzyl alcohol, 2-(3,4,5-Trimethoxyphenyl)-1-ethanol, and 3-(2,5-Dimethoxyphenyl)-propan-1-ol, respectively.

Example 23

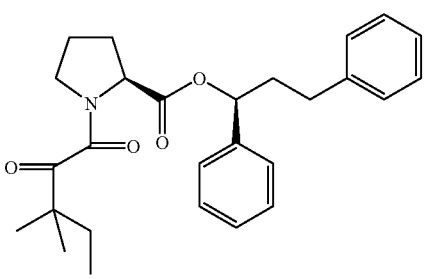

(1S)-1,3-Diphenyl-1-propyl (2S)-1-(3,3-dimethyl-1,2-dioxopentyl)-2-pyrrolidinecarboxylate.

¹H NMR (CDCl₃; 360 MHz): δ 0.87 (t, 3H); 1.20 (s, 3H); 1.24 (s, 3H); 1.62–2.32 (m, 8H); 2.62–2.75 (m, 2H); 3.43–3.60 (m, 2H); 4.58–4.73 (m, 1H); 5.76 (td, 1H, J=1.8, 6.7); 7.19 (m, 3H); 7.24–7.35 (m, 7H).

Example 23 was prepared according to the synthetic procedure outlined for Examples 1–3, except that the requisite optically active 1-substituted alkanol in the reaction mixture was (1S)-1,3-Diphenylpropan-1-ol.

Example 24

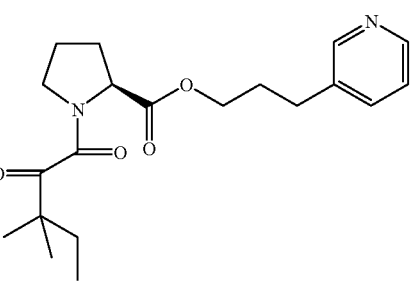

3-(3-Pyridyl)-1-propyl (2S)-1-(3,3-dimethyl-1,2-dioxopentyl)-2-pyrrolidinecarboxylate.

¹H NMR (CDCl₃; 360 MHz): δ 0.85 (t, 3H); 1.23,1.26 (s, 3H each); 1.69–1.90 (m, 3H); 1.95–2.01 (m, 4H); 2.20 (m, 1H); 2.72 (t, 2H); 3.53 (m, 2H); 4.18 (m, 2H); 4.52 (m, 1H); 7.22 (m, 1H); 7.53 (dd, 1H); 8.45 (m, 2H).

Example 24 was prepared according to the synthetic procedure outlined for Examples 1–3, except that the requisite alcohol in the reaction mixture was 3-(3-Pyridyl)-propan-1-ol. Example 24 is compound 23 in Tables I and III.

Example 25

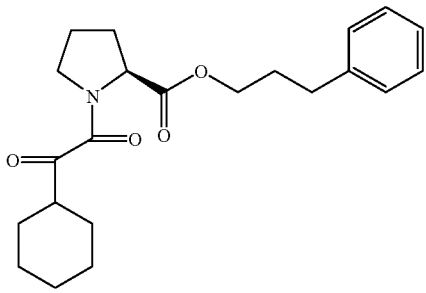

3-Phenyl-1-propyl (2S)-1-(cyclohexylglyoxyl)-2-pyrrolidinecarboxylate.

$^1$H NMR (CDCl$_3$; 300 MHz): δ 1.09–1.33 (m, 5H); 1.62–2.33 (m, 12H); 2.69 (t, 2H, J=7.5); 3.15 (dm, 1H); 3.68 (m, 2H); 4.16 (m, 2H); 4.53, 4.84 (d, 1H total); 7.19 (m, 3H); 7.29 (m, 2H). Example 25 is compound 24 in Tables I and III.

Example 26

The requisite substituted alcohols may be prepared by a number of methods known to those skilled in the art of organic synthesis. As described in Scheme II, alkyl or aryl aldehydes may be homologated to phenyl propanols by reaction with methyl (triphenylphosphoranylidene) acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

Scheme II

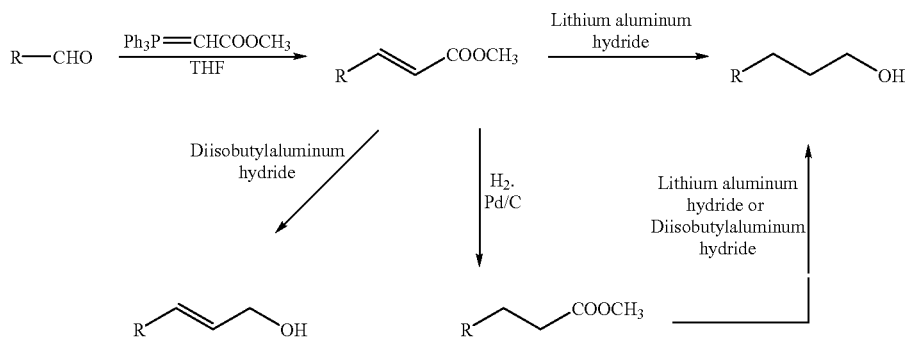

Longer chain alcohols may be prepared by homologation of benzylic and higher aldehydes. Alternatively, these aldehydes may be prepared by conversion of the corresponding phenylacetic and higher acids, and phenethyl and higher alcohols.

Example 27

General procedure for the synthesis of acrylic esters, exemplified for methyl (3,3,5-trimethoxy)-trans-cinnamate:

A solution of 3,4,5-trimethoxybenzaldehyde (5.0 g; 25.48 mmol) and methyl (triphenyl-phosphoranylidene)acetate (10.0 g; 29.91 mmol) in tetrahydrofuran (250 mL) was refluxed overnight. After cooling, the reaction mixture was diluted with 200 mL of ethyl acetate and washed with 2×200 mL of water, dried, and concentrated in vacuo. The crude residue was chromatographed on a silica gel column, eluting with 25% ethyl acetate in hexane, to obtain 5.63 g (88%) of the cinnamate as a white crystalline solid, hu 1H NMR (300 Mhz; CDCl$_3$): δ 3.78 (s, 3H); 3.85 (s, 6H); 6.32 (d, 1H, J=16); 6.72 (s, 2H); 7.59 (d, 1H, J=16).

Example 28

Methyl (4,5-dichloro)-trans-cinnamate, 80%, $^1$H NMR (300 Mhz; CDCl$_3$): δ 3.79 (s, 3H); 6.40 (d, 1H, J=16.8); 7.32 (dd, 1H, J=1.5, 8.1); 7.44 (d, 1H, J=8.1); 7.56 (d, 1H, J=16); 7.58 (s, 1H). This compound was prepared by the method of Example 27 from 3,4,5-trimethoxybenzaldehyde.

Example 29

Methyl (4,5-methylenedioxy)-trans-cinnamate, 74%, $^1$H NMR (360 Mhz; CDCl$_3$): δ 3.79 (s, 3H); 6.01 (s, 2H); 6.26 (d, 1H, J=16); 6.81 (d, 1H, J=7.9); 7.00 (d, 1H, J=8.2); 7.03 (s, 1H); 7.60 (d, 1H, J=16). This compound was prepared by the method of Example 27 from 3,4,5-trimethoxybenzaldehyde.

Example 30

Methyl (2-cyclohexyl)-(E)-acrylate, 80%, $^1$H NMR (360 Mhz; CDCl$_3$): δ 1.12–1.43 (m, 5H); 1.52–1.87 (m, 5H); 2.12 (m, 1H); 2.12 (m, 1H); 3.71 (s, 3H); 5.77 (dd, 1H, J=1.2, 15.8); 6.92 (dd, 1H, j=6.8, 15.8). This compound was prepared by the method of Example 27 from 3,4,5-trimethoxybenzaldehyde.

Example 31

General procedure for the synthesis of saturated alcohols from acrylic esters. Exemplified for (3,4,5-trimethoxy)phenylpropanol.

A solution of methyl (3,3,5-trimethoxy)-trans-cinnamate (1.81 g; 7.17 mmol) in tetrahydrofuran (30 mL) was added in a dropwise manner to a solution of lithium aluminum hydride (14 mmol) in THF (35 mL), with stirring and under an argon atmosphere. After the addition was complete, the mixture was heated to 75° C. for 4 hours. After cooling, it was quenched by the careful addition of 15 mL of 2N NaOH followed by 50 mL of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil, $^1$H NMR (300 Mhz; CDCl$_3$): δ 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

Example 32

General procedure for the synthesis of trans-allylic alcohols from acrylic esters. Exemplified for (3,4,5-trimethoxy) phenylprop-2-(E)-enol.

A solution of methyl (3,3,5-trimethoxy)-trans-cinnamate (1.35 g; 5.35 mmol) in toluene (25 mL) was cooled to –10° C. and treated with a solution of diisobutylaluminum hydride in toluene (11.25 mL of a 1.0 M solution; 11.25 mmol). The reaction mixture was stirred for 3 hrs at 0° C. and then quenched with 3 mL of methanol followed by 1 N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil, $^1$H NMR (360 Mhz; CDCl$_3$): δ 3.85 (s, 3H); 3.87 (s, 6H); 4.32 (d, 2H, J=5.6); 6.29 (dt, 1H, J=15.8, 5.7), 6.54 (d, 1H, J=15.8); 6.61 (s, 2H).

Example 33

(4,5-dichloro)phenylprop-2-(E)-enol, 89%, $^1$H NMR (360 Mhz; CDCl$_3$): δ 1.55 (s, 3H); 4.34 (d, 2H, J=4.4); 6.36 (dt, 1H, J=15.9, 5.3); 6.54 (d, 1H, J=15.9); 7.20 (dd, 1H, J=8.3, 1.7); 7.38 (d, 1H. J=8.3); 7.45 (d, 1H, J=1.6). This compound was prepared by the method of Example 32 from 3,4,5-(trimethoxy)-trans-cinnamate.

Example 34

(4,5-methylenedioxy)phenylprop-2-(E)-enol, 80%, $^1$H NMR (360 Mhz; CDCl$_3$): δ 1.59 (br, 1H); 4.29 (br, 2H); 5.96 (s, 2H); 6.20 (dt, 1H, J=15.8, 5.9); 6.52 (d, 1H, J=15.8); 6.76 (d, 1H, J=8.0); 6.82 (dd, 1H, J=8.0, 1.2); 6.93 (d, 1H, J=1.2). This compound was prepared by the method of Example 32 from 3,4,5-(trimethoxy)-trans-cinnamate.

Example 35

Phenylprop-2-(E)-enol, 85%, $^1$H NMR (360 Mhz; CDCl$_3$): δ 1.72 (br, 1H); 4.31 (d, 2H, J=5.7); 6.36 (dt, 1H, J=15.9, 5.7); 6.61 (d, 1H, J=15.9); 7.02–7.55 (m, 5H). This compound was prepared by the method of Example 32 from 3,4,5-(trimethoxy)-trans-cinnamate.

Example 36

Alcohols containing a substituent at the 1-position of the side chain may be conveniently prepared by addition of appropriate nucleophiles to aldehydes, as described in Scheme III. In cases where optically active substituted alcohols are desired, the racemic alcohols may be oxidized to prochiral ketones and subjected to asymmetric reduction by one of several methods well known to those skilled in the art.

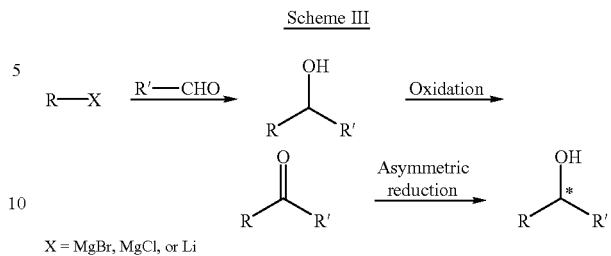

Scheme III

X = MgBr, MgCl, or Li

Example 37

General procedure for the preparation of 1-substituted alkanols, exemplified for the synthesis of 1,3-diphenylpropanol.

A solution of 2-(bromoethyl)benzene (17.45 g; 94.3 mmol) in 50 mL of dry diethyl ether was added dropwise, under a nitrogen atmosphere, to a stirred slurry of magnesium turnings (2.50 g; 102.8 mmol) in 50 mL of ether. The mixture was initially heated with a heat gun until reflux had become self-sustaining. After the addition was complete, the mixture was heated externally for 30 min to maintain reflux. A solution of 10.01 g (94.3 mmol) of benzaldehyde in 20 mL of ether was then added dropwise, and reflux was continued for 30 min. After cooling, the reaction mixture was poured into 150 mL of saturated ammonium chloride and extracted into ethyl acetate. The crude material obtained upon removal of the solvent was purified on a flash column, eluting with 5% ethyl acetate/hexane to 20% ethyl acetate, to obtain 13.73 g (69%) of the alkanol as a light yellow oil, $^1$H NMR (360 Mhz; CDCl$_3$): δ 1.93–2.30 (m, 3H); 2.70–2.90 (m, 2H); 4.72 (br, 1H); 7.19–7.27 (m, 3H); 7.27–7.36 (m, 3H); 7.36–7.47 (m, 4H).

Example 38

General procedure for conversion of racemic 1-substituted alkanols to optically active 1-substituted alkanols via prochiral ketones. Exemplified for (1R)-1,3-diphenyl-1-propanol.

A solution of racemic 1,3-diphenyl-1-propanol (1,26 g; 5.94 mmol) was dissolved in 10 mL of acetone, and Jones reagent was added until persistence of the orange color. After stirring for 30 min, the reaction was quenched by adding 2 mL of 2-propanol. The solvent was decanted away from the precipitated solids, which were washed with ethyl acetate. The combined organic fractions were washed with 2×20 mL of water, dried and concentrated. The crude product was filtered through a plug of silica gel, eluting with 25% ethyl acetate/hexane, to obtain 1.07 g (86%) of 1,3-diphenylpropanone as a white crystalline solid, $^1$H NMR (360 Mhz; CDCl$_3$): δ 3.09 (t, 2H, J=8.1); 3.33 (t, 2H, J=8.1); 7.29 (m, 5H); 7.49 (m, 3H); 7.98 (m, 2H).

A solution of 1,3-diphenylpropanone (1.07 g; 5.09 mmol) in tetrahydrofuran (10 mL) was cooled to –23° C. and treated with an asymmetric reducing agent, (+)-B-chlorodiisopinocampheyl-borane (1.80 g; 5.60 mmol) in 20 mL THF, and the resulting solution was allowed to stand overnight at –23° C. After evaporating to dryness, the residue was treated with ether (65 mL) and diethanolamine (1.0 g) and stirred for 3 hrs. The mixture was then filtered to remove solids and concetrated, and the residue was purified using gradient elution (5% ethyl acetate/hexane to 10% ethyl acetate) on a silica gel column to obtain 660 mg (61%) of (1R)-1,3-diphenyl-1-propanol as a crystalline white solid, $^1$H NMR (360 Mhz; CDCl$_3$): δ 1.95–2.15 (m, 3H); 2.59–2.78 (m, 2H); 4.65 (dd, 1H, J=5.4, 7.8); 7.14–7.35 (m, 10H).

Scheme IV

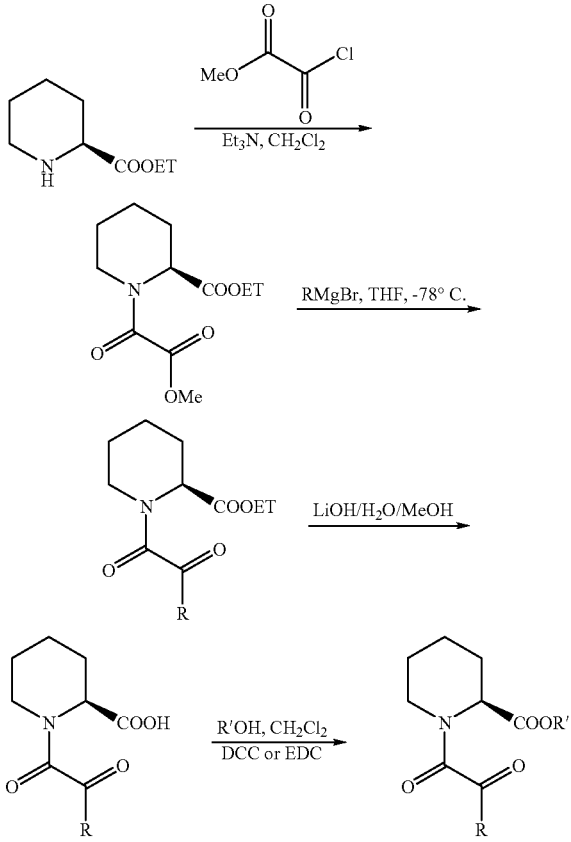

Example 39

Synthesis of ethyl 1-(1,2-dioxo-2-methoxyethyl)-2-piperidinecarboxylate.

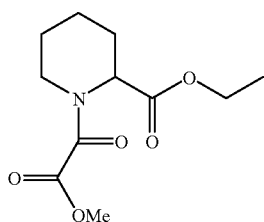

A solution of ethyl pipecolinate (1.00 g; 5.57 mmol) in dry methylene chloride (15 mL) was cooled to 0° C. and treated with triethylamine (1.24 g; 12.25 mmol; 2.1 eq). After stirring the formed slurry under a nitrogen atmosphere for 15 min, a solution of methyl oxalyl chloride (0.96 g; 6.13 mmol) in methylene chloride (15 mL) was added dropwise. The resulting mixture was stirred at 0° C. for 1.5 hr. After filtering to remove solids, the organic phase was washed with water, dried over MgSO$_4$ and concentrated. The crude residue was purified on a silica gel column, eluting with 50% ethyl acetate in hexane, to obtain 1.21 g (95%) of the product as a reddish oil. Mixture of cis-trans amide rotamers; data for trans rotamer given. $^1$H NMR (300 MHz, CDCl$_3$): δ 1.25 (t, 3H); 1.30–1.75 (m, 5H); 2.33 (m, 1H); 3.42 (dt, 1H); 3.57 (br d, 1H); 3.85 (s, 3H); 4.29 (dd, 2H); 5.23 (d, 1H).

Example 40

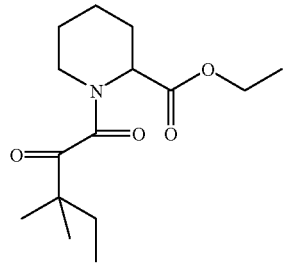

Synthesis of ethyl 1-(1,2-dioxo-3,3-dimethylpentyl)-2-piperidinecarboxylate.

A solution of ethyl 1-(1,2-dioxo-2-methoxyethyl)-2-piperidinecarboxylate (1.43 g; 5.88 mmol) in 20 mL of tetrahydrofuran (THF) was cooled to −78° C. and treated with 8 mL of a 1.0 M solution of 1,1-dimethylpropylmagnesium chloride in THF. After stirring the resulting homogeneous mixture at −78° C. for three hours, the mixture was poured into saturated ammonium chloride (30 mL) and extracted into ethyl acetate. The organic phase was washed with water, dried, and concentrated, and the crude material obtained upon removal of the solvent was purified on a silica gel column, eluting with 25% ethyl acetate in hexane, to obtain 1.35 g (76%) of the oxamate as a colorless oil. $^1$H NMR (300 MHz, CDCl$_3$): δ 0.91 (t, 3H); 1.20,1.25 (s, 3H each); 1.30 (t, 3H); 1.35–1.80 (m, 7H); 2.35 (br d, 1H); 3.20 (td, 1H); 3.41 (br d, 1H); 4.20 (q, 2H); 5.22 (d, 1H).

Example 41

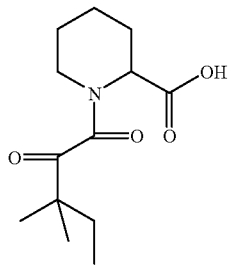

Synthesis of 1-(1,2-dioxo-3,3-dimethylpentyl)-2-piperidinecarboxylic acid

A mixture of ethyl 1-(1,2-dioxo-3,3-dimethylpentyl)-2-piperidinecarboxylate (0.69 g; 2.43 mmol), 1 N LiOH (5 mL), and methanol (20 mL) was stirred at 0° C. for 30 min and at room temperature overnight. The mixture was acidified to pH 1 with 1 N HCl, diluted with water, and extracted into 50 mL of methylene chloride. The organic extract was washed with brine and concentrated to deliver 0.61 g (98%) of snow-white solid which did not require further purification.

Example 42

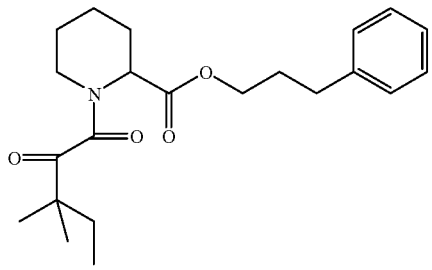

Synthesis of 3-Phenyl-1-propyl 1-(1,2-dioxo-3,3-dimethylpentyl)-2-piperidinecarboxylate A mixture of 1-(1,2-dioxo-3,3-dimethylpentyl)-2-piperidinecarboxylic acid (590 mg; 2.31 mmol), 3-phenylpropanol (520 mg; 3.71 mmol), dicyclohexylcarbodiimide (815 mg; 3.95 mmol), camphorsulphonic acid (180 mg; 0.77 mmol) and 4-dimethyl aminopyridine (95 mg; 0.77 mmol) in methylene chloride (15 mL) was stirred overnight under a nitrogen atmosphere. The reaction mixture was filtered through Celite to remove solids and concentrated in vacuo. The crude material was triturated with several portions of ether, and the ether portions were filtered through Celite to remove solids and concentrated in vacuo. The concentrated filtrate was purified on a flash column (20% ethyl acetate in hexane) to obtain 800 mg (93%) of the product as an oil, $^1$H NMR (CDCl$_3$, 300 MHz): δ 0.85 (t, 3H); 1.23,1.26 (s, 3H each); 1.63–1.94 (m, 9H); 2.32 (m, 1H); 2.69 (m, 2H); 3.21 (m, 1H); 3.35 (m, 1H); 4.17 (m, 2H); 5.24 (m, 1H); 7.14 (m, 3H); 7.7.23 (m, 2H).

The following compounds were prepared by this method:

Example 43

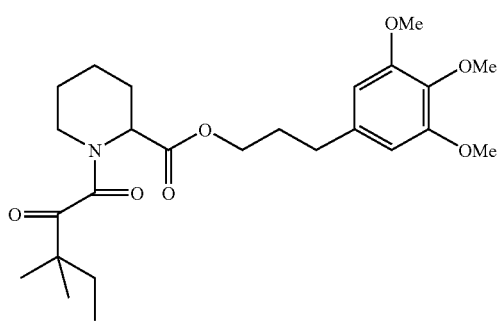

3-(3,4,5-Trimethoxyphenyl)-1-propyl 1-(3,3-dimethyl-1,2-dioxopentyl)-2-piperidinecarboxylate: $^1$H NMR (CDCl$_3$, 300 MHz): δ 0.80 (t, 3H); 1.18 (s, 6H); 1.67 (m, 7H); 1.94 (m, 2H); 2.29 (br d, 1H); 2.61 (t, 2H); 3.17 (td, 1H); 3.35 (d, 1H); 3.79 (s, 3H); 3.81 (s, 6H); 4.15 (m, 2H); 5.24 (d, 1H).

Example 44

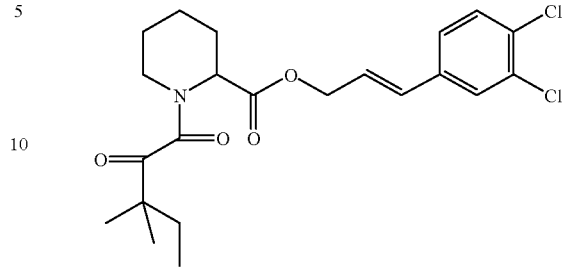

3-(4,5-Dichlorophenyl)-1-prop-2-(E)-enyl 1-(3,3-dimethyl-1,2-dioxopentyl)-2-piperidinecarboxylate: $^1$H NMR (CDCl$_3$, 360 MHz): δ 0.89 (t, 3H); 1.18 (s, 3H); 1.24 (s, 3H); 1.57–1.89 (m, 7H); 2.38 (d, 1H); 3.20–3.28 (dt, 1H); 3.30–3.43 (dm, 1H); 4.81 (d, 2H); 5.31 (d, 1H); 6.16–6.36 (m, 1H); 6.48–6.68 (d, 1H); 7.20 (d, 1H); 7.3 (d, 1H); 7.47 (s, 1H).

Example 45

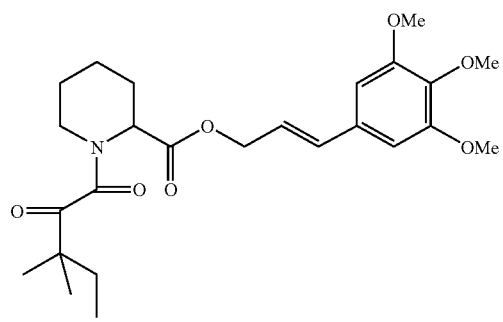

3-(3,4,5-Trimethoxyphenyl)-1-prop-2-(E)-enyl 1-(3,3-dimethyl-1,2-dioxopentyl)-2-piperidinecarboxylate: $^1$H NMR (CDCl$_3$, 360 MHz): δ 0.89 (t, 3H); 1.21 (s, 3H); 1.24 (s, 3H); 1.41–1.85 (m, 7H); 2.35 (d, 1H); 3.25 (t, 1H); 3.39 (m, 1H); 3.86 (s, 3H); 3.89 (s, 6H); 4.81 (m, 2H); 5.33 (d, 1H); 6.21 (m, 1H); 6.61 (d, 1H); 6.63 (s, 2H).

Example 46

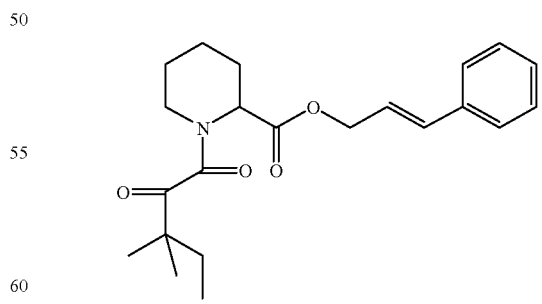

3-Phenyl-1-prop-2-(E)-enyl 1-(3,3-dimethyl-1,2-dioxopentyl)-2-piperidinecarboxylate: $^1$H NMR (CDCl$_3$, 360 MHz): δ 0.88 (t, 3H); 1.20 (s, 3H); 1.24 (s, 3H); 1.25–1.77 (m, 6H); 1.86–2.06 (m, 1H); 2.30–2.40 (m, 1H): 3.24 (t, 1H); 3.41 (d, 1H); 4.82 (d, 1H); 5.31 (d, 1H); 6.25–6.29 (m, 1H); 6.68 (d, 1H); 7.26–7.54 (m, 5H).

Example 47

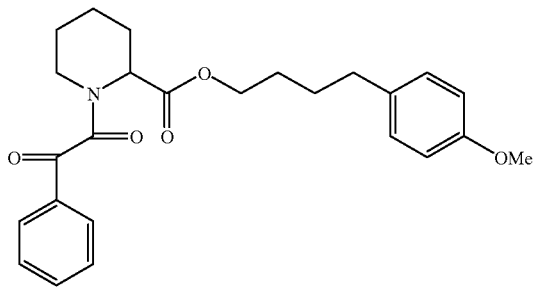

4-(4-Methoxyphenyl)butyl N-(phenylglyoxyl))-2-piperidinecarboxylate: $^1$H NMR (CDCl$_3$, 300 MHz): δ 1.26–1.78 (m, 9H); 2.36 (d, 1H); 2.58 (m, 2H); 3.25 (m, 1H); 3.48 (dm, 1H); 3.78 (s, 3H); 4.24 (m, 2H); 5.40 (m, 1H); 6.82 (d, 2H); 7.09 (d, 2H); 7.64 (m, 2H); 7.66 (m, 1H); 8.02 (m, 2H). Anal. Calcd. for C$_{25}$H$_{29}$NO$_5$: C, 70.90; H, 6.90; N, 3.31. Found: C, 70.87; H, 6.92; N, 3.36. Example 47 is compound 3 in Tables I and III.

Example 48

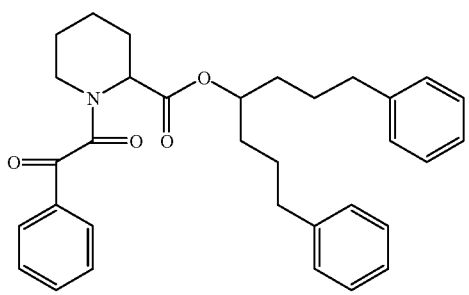

1,7-Diphenylheptanyl N-(phenylglyoxyl))-2-piperidinecarboxylate: $^1$H NMR (CDCl$_3$, 300 MHz): δ 1.21–1.85 (m, 14H); 2.48 (m, 4H); 3.22 (m, 1H); 3.44 (m, 1H); 5.09 (br, 1H); 5.38 (br, 1H); 7.06–8.04 (m, 15H). Anal. Calcd. for C$_{33}$H$_{37}$NO$_4$: C, 77.47; H, 7.29; N, 2.74. Found: C, 77.39; H, 7.32; N, 2.66. Example 48 is compound 20 in Tables I and III.

Example 49

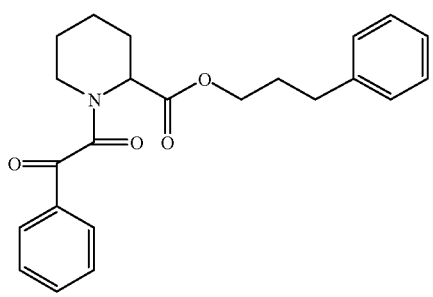

3-Phenyl-1-propyl N-(phenylglyoxyl))-2-piperidinecarboxylate: $^1$H NMR (CDCl$_3$, 300 MHz): δ 1.36–2.05 (m, 7H); 2.36 (d, 1H); 2.74 (m, 2H); 3.24 (t, 1H); 3.50 (t, 1H); 4.25 (m, 2H); 5.42 (m, 1H); 7.28 (m, 4H); 7.64 (m, 4H); 8.03 (m, 2H). Anal. Calcd. for C$_{23}$H$_{25}$NO$_4$: C, 72.80; H, 6.64; N, 3.69. Found: C, 72.74; H, 6.62; N, 3.62. Example 49 is compound 2 in Tables I and III.

Example 50

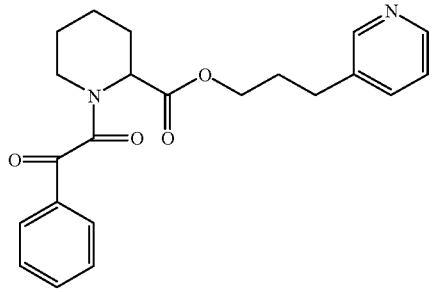

3-(3-Pyridyl)-1-propyl N-(phenylglyoxyl))-2-piperidinecarboxylate: $^1$H NMR (CDCl$_3$, 300 MHz): δ 1.26–2.08 (m, 7H); 2.35 (d, 1H); 2.75 (t, 2H); 3.29 (t, 1H); 3.49 (d, 1H); 4.27 (t, 2H); 5.42 (d, 1H); 7.23 (m, 1H); 7.52 (m, 3H); 7.63 (m, 1H); 8.03 (m, 2H); 8.48 (m, 2H). Anal. Calcd. for C$_{22}$H$_{24}$N$_2$O$_4$·0.25H$_2$O: C, 68.64; H, 6.42; N, 7.28. Found: C, 68.37; H, 6.41; N, 7.22.

Example 51

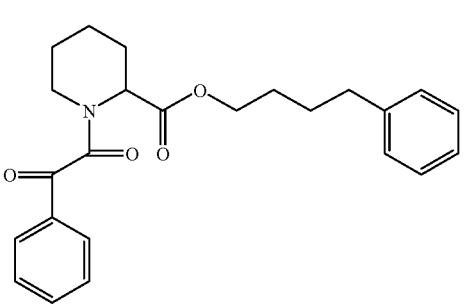

4-Phenyl-1-butyl N-(phenylglyoxyl))-2-piperidinecarboxylate: $^1$H NMR (CDCl$_3$, 300 MHz): δ 1.26–1.80 (m, 12H); 2.67 (m, 2H); 3.23 (t, 1H); 3.49 (t, 1H); 4.25 (m, 2H); 5.40 (m, 1H); 7.18 (m, 3H); 7.26 (m, 2H); 7.48 (m, 2H); 7.64 (m, 1H); 8.03 (m, 2H). Anal. Calcd. for C$_{24}$H$_{27}$NO$_4$: C, 73.26; H, 6.92; N, 3.56. Found: C, 73.19; H, 6.94; N, 3.64. Example 51 is compound 4 in Tables I and III.

Example 52

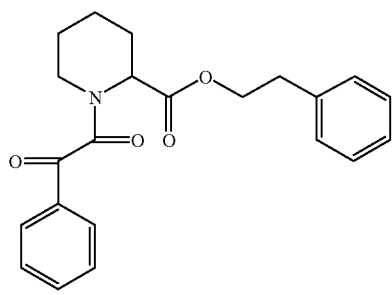

2-Phenyl-1-ethyl N-(phenylglyoxyl))-2-piperidinecarboxylate: $^1$H NMR (CDCl$_3$, 300 MHz): δ 1.23–1.75 (m, 5H); 2.21 (d, 1H); 3.09 (m, 3H); 3.41 (d, 1H); 4.48 (m, 2H); 5.38 (m, 1H); 7.27 (m, 5H); 7.53 (m, 2H); 7.65 (m, 1H); 8.01 (m, 2H). Anal. Calcd. for $C_{22}H_{23}NO_4 \cdot 0.25H_2O$: C, 71.43; H, 6.40; N, 3.79. Found: C, 71.60; H, 6.50; N, 4.12. Example 52 is compound 5 in Tables I and III.

Example 53

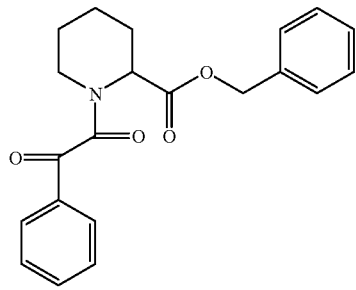

Benzyl N-(phenylglyoxyl)-2-piperidinecarboxylate: $^1$H NMR (CDCl$_3$, 300 MHz): δ1.38–1.81 (m, 5H); 2.41 (d, 1H); 3.22 (m, 1H); 3.48 (d, 1H); 5.26 (s, 2H); 5.47 (d, 1H); 7.42 (m, 7H); 7.61 (m, 1H); 7.97 (m, 2H). Anal. Calcd. for $C_{21}H_{21}NO_4 \cdot 0.25H_2O$: C, 71.78; H, 6.02; N, 3.99. Found: C, 71.90; H, 6.12; N, 4.01. Example 53 is compound 1 In Tables I and III.

Example 54

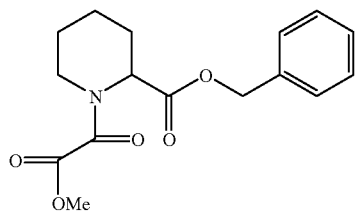

Benzyl N-(methoxyglyoxyl)-2-piperidinecarboxylate: $^1$H NMR (CDCl$_3$, 300 MHz): δ 1.26–1.77 (m, 5H); 2.32 (m, 1H); 3.33 (t, 1H); 3.54 (d, 1H); 3.88 (s, 3H); 5.23 (s, 2H); 5.45 (m, 1H); 7.36 (s, 5H). Anal. Calcd. for $C_{16}H_{19}NO_5$: C, 62.94; H, 6.27; N, 4.59. Found: C, 62.80; H, 6.35; N, 4.53.

Scheme V

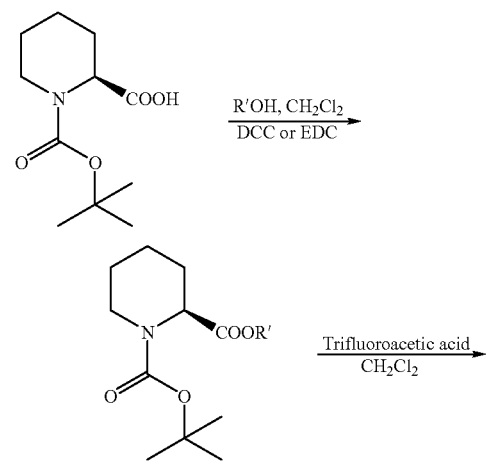

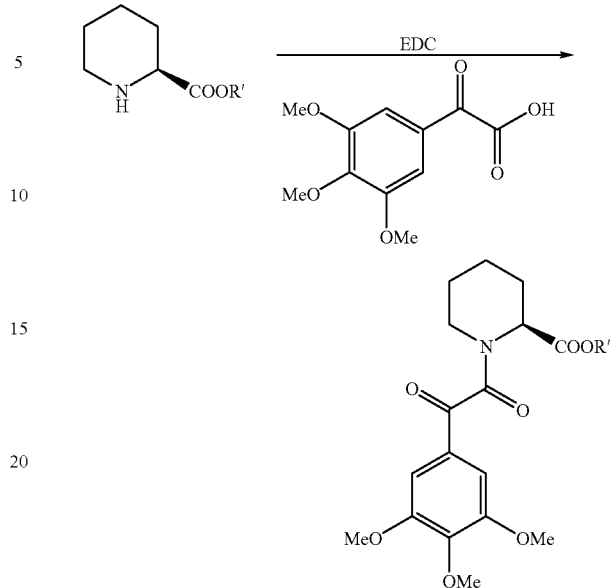

Example 55

Synthesis of (S)-Boc-pipecolyl-1,7-diphenyl-4-heptanyl ester:

A solution of (S)-boc-pipecolic acid (330 mg; 1.44 mmol) in CH$_2$Cl$_2$ (20 mL) was treated with 1,7-diphenyl-4-heptanol (350 mg; 1.30 mmol), 1-(3-dimethylaminopropyl)-3-ethylcarbodiimide hydrochloride (280 mg; 1.44 mmol), and a catalytic amount of N,N,-dimethylaminopyridine. The reaction mixture was stirred overnight at room temperature, concentrated, and purified on a silica gel column eluting with 25% ethyl acetate in hexanes to provide 160 mg of product as a clear oil.

(S)-1,7-diphenyl-4-heptanylpipecolate: A solution of (S)-boc-pipecolyl-1,7-diphenyl-4-heptanyl ester (150 mg) in 10 ml of CH$_2$Cl$_2$ was treated with 3 mL of trifluoroacetic acid and stirred at room temperature for 2 hours. It was neutralized with aqueous potassium carbonate and the layers were separated. The organic phase was dried over MgSO$_4$ and concentrated to provide 70 mg of the free amine.

Example 56

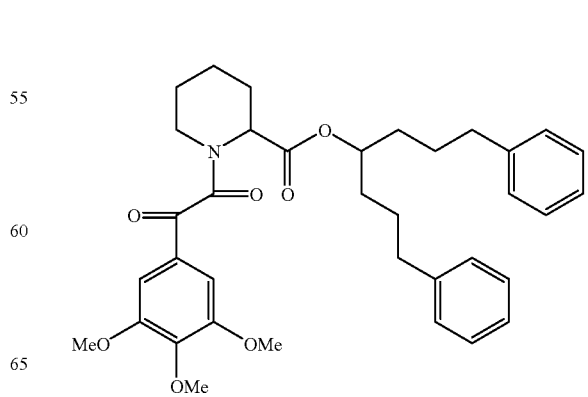

1,7-Diphenyl-4-heptyl (S)-N-(3,4,5-trimethoxyphenylglyoxyl)pipecolate: A solution of (S)-1,7-diphenyl-4-heptanylpipecolate (50 mg; 0.13 mmol) and 3,4,5-trimethoxybenzoyl-formic acid (45 mg; 0.2 mmol) was treated with 1-(3-dimethylaminopropyl)-3-ethyl-carbodiimide hydrochloride (40 mg; 0.2 mmol) and a catalytic amount of N,N,-dimethylaminopyridine. The reaction mixture was stirred overnight at room temperature, concentrated, and purified on a silica gel column eluting with 25% ethyl acetate in hexanes to provide 20 mg of product as a clear oil, $^1$H NMR (300 MHz; CDCl$_3$): δ 1.31–1.92 (m, 13H); 2.35 (m, 1H); 2.66 (m, 4H); 3.29 (td, 1H); 3.94 (s, 9H); 5.08 (m, 1H); 5.41 (d, 1H); 7.19 (m, 6H); 7.28 (m, 4H); 7.42 (m, 2H). Example 56 is compound 21 in Tables I and III.

The following compounds were prepared by the method of Scheme V:

Example 57

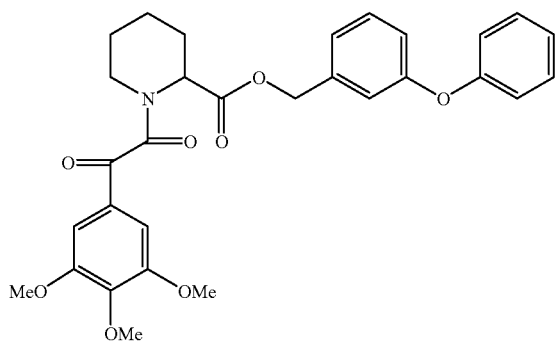

3-(Phenoxybenzyl) (S)-N-(3,4,5-trimethoxyphenylglyoxyl)pipecolate: $^1$H NMR (300 MHz; CDCl$_3$): δ 1.22–1.47 (m, 1H); 1.50–1.70 (m, 2H); 1.72–1.93 (m, 2H); 2.39 (d, 1H); 3.25 (td, 1H); 3.51 (d, 1H); 3.96 (s, 9H); 5.18 (m, 2H); 5.43 (d, 1H); 7.01 (4H); 7.15 (m, 3H); 7.37 (m, 4H). Example 57 is compound 13 in Tables I and III.

Example 58

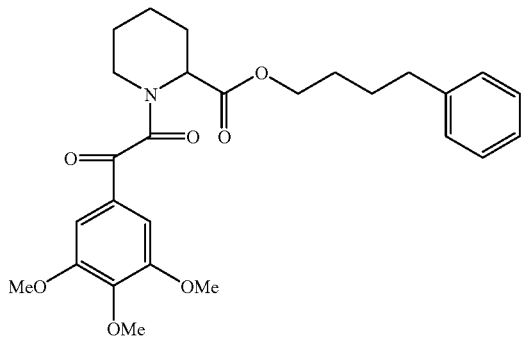

4-Phenylbutyl (S)-N-(3,4,5-trimethoxyphenylglyoxyl)pipecolate: $^1$H NMR (300 MHz; CDCl$_3$): δ 1.32–1.88 (m, 9H); 2.35 (d, 1H); 2.63 (m, 2H); 3.25 (td, 1H); 3.48 (d, 1H); 3.93 (s, 9H); 4.18 (m, 2H); 5.35 (d, 1H); 7.17 (m, 3H); 7.23 (m, 2H); 7.36 (s, 2H). Example 58 is compound 14 in Tables I and III.

Example 59

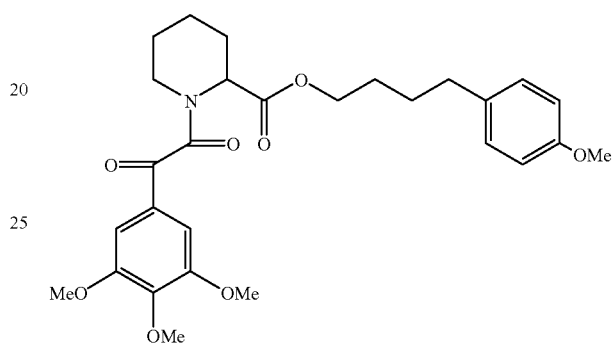

4-(4-Methoxyphenyl)butyl (S)-N-(3,4,5-trimethoxyphenylglyoxyl)pipecolate: $^1$H NMR (300 MHz; CDCl$_3$): δ 1.21–1.92 (m, 9H); 2.37 (m, 1H); 2.62 (m, 2H); 3.25 (td, 1H); 3.49 (d, 1H); 3.78 (s, 3H); 3.93 (s, 9H); 4.15–4.23 (m, 2H); 5.38 (m, 1H); 6.39 (m, 2H); 7.07 (m, 1H); 7.36 (m, 1H). Example 59 is compound 16 in Tables I and III.

Example 60

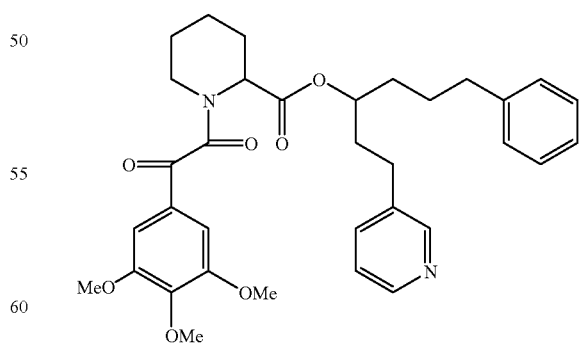

1-Phenyl-6-(3-pyridyl)-3-hexyl (S)-N-(3,4,5-trimethoxyphenylglyoxyl)pipecolate: $^1$H NMR (300 MHz; CDCl$_3$): δ

1.22–2.01 (m, 11H); 2.39 (m, 1H); 2.65 (m, 4H); 3.32 (m, 1H); 3.53 (m, 1H); 3.92 (s, 9H); 5.06 (m, 1H); 5.40 (dd, 1H); 7.17–7.32 (m, 6H); 7.37 (d, 2H); 7.50 (m, 1H); 8.48 (m, 2H). Example 60 is compound 22 in Tables I and III.

Example 61

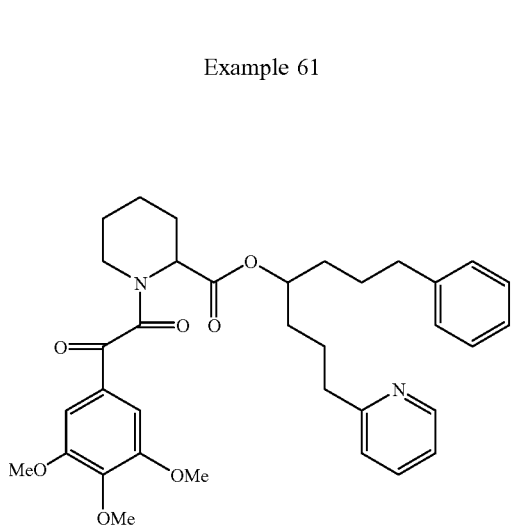

1-Phenyl-7-(2-pyridyl)-4-heptyl (S)-N-(3,4,5-trimethoxyphenylglyoxyl)pipecolate: $^1$H NMR (300 MHz; CDCl$_3$): δ 1.23–2.02 (m, 13H); 2.39 (d, 1H); 2.65 (m, 2H); 2.86 (t, 2H); 3.31 (t, 1H); 3.51 (d, 1H); 3.94 (s, 9H); 5.10 (m, 1H); 5.40 (m, 1H); 7.16–7.32 (m, 9H); 7.61 (7, 1H); 8.51 (m, 1H). Example 61 is compound 23 in Tables I and III.

Example 62

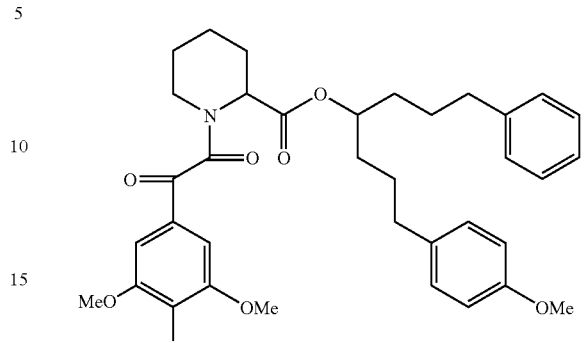

1-Phenyl-7-(4-methoxyphenyl)-4-heptyl (S)-N-(3,4,5-trimethoxyphenylglyoxyl)-pipecolate: $^1$H NMR (300 MHz; CDCl$_3$): δ 1.22–1.88 (m, 13H); 2.32 (d, 1H); 2.60 (m, 4H); 3.25 (td, 1H); 3.48 (d, 1H); 3.76 (s, 3H); 3.91 (s, 9H); 5.05 (m, 1H); 5.37 (m, 1H); 6.80 (d, 2H); 7.00–7.11 (m, 2H); 7.13–7.20 (m, 3H); 7.21–7.28 (m, 2H); 7.4 (s, 2H). Example 62 is compound 24 in Tables I and III.

Example 63

Synthesis of Piperidine Ketone Compounds

Scheme VI

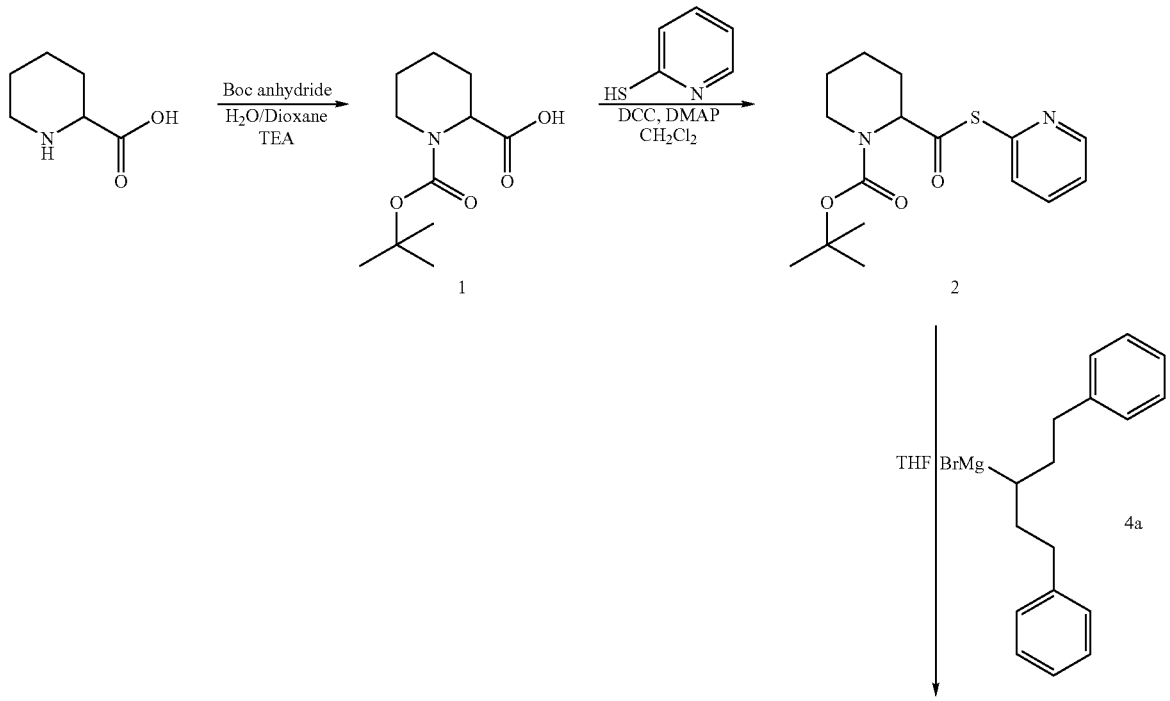

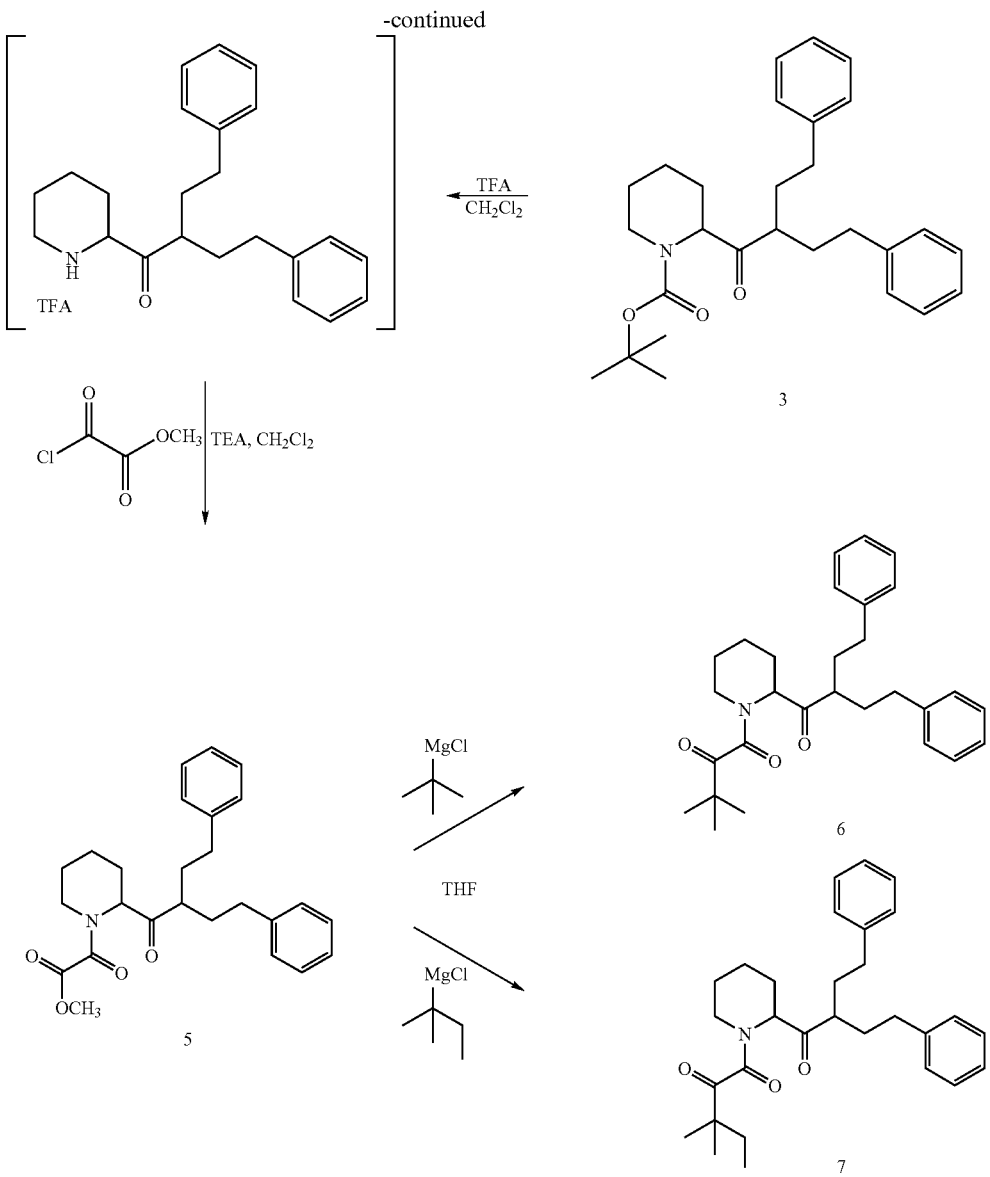

Piperidine-1,2-dicarboxylic acid 1-tert-butyl ester (1). To a solution of 10.0 g (77.42 mmol) of piperidine-2-carboxylic acid in H₂O/Dioxane (200 mL, 1:1) was added 18.59 g (85.16 mmol) of di-tert-butyl dicarbonate followed by 8.62 g (85.16 mmol) of triethyl amine, and the mixture was stirred for 16 hrs at ambient temperature. The solution was evaporated to remove excess dioxane, diluted with H₂O (100 mL) and extracted with CH₂Cl₂ (2×200 mL). The organic phase was dried (MgSO₄) and the evaporated to give a yellow oil which was subject to column chromatography (CHCl₃/MeOH/AcOH, 9:0.8:0.2) to yield 12.9 g (73.0%) of 1 as a yellow oil. TLC $R_f$=0.7 (CHCl₃/MeOH/AcOH, 9:0.8: 0.2)

2-(Pyridin-2-ylsulfanylcarbonyl)-piperidine-1-carboxylic acid tert-butyl ester (2). To a solution of 12.9 g (56.51 mmol) of 1 and 17.49 g (84.77 mmol) of 1,3-dicyclohexylcarbodiimide in CH₂Cl₂ (250 mL) was added 9.42 g (84.77 mmol) of pyridine-2-thiol followed by 0.25 g (0.2 mmol) of 4-dimethylaminopyridine, and the mixture was stirred for 16 hrs at ambient temperature. The slurry was filtered and the resulting organic phase was evaporated to yield a yellow oil which was subject to column chromatography (EtOAc/Hexanes, 3:2) to yield 11.2 g (61.5%) of 2 as a yellow oil. TLC $R_f$=0.6 (EtOAc/Hexanes, 3:2)

2-(2-Phenethyl-4-phenyl-butyryl)-piperidine-1-carboxylic acid tert-butyl ester (3). To a solution of 0.95 g (2.95 mmol) of 2 in anhydrous THF (12 mL) was added dropwise at 0° C. a solution of 5.4 mL (3.24 mmol) of 4a over 5 minutes. After 2 hours at 0° C., the solution was allowed to warm to an ambient temperature for 18 hrs. The solution was quenched with H₂O and extracted with ether (3×50 mL). The organic phase was washed with brine, dried (MgSO₄) and evaporated to a clear oil which was subject to column chromatography (EtOAc/Hexanes, 0.5:9.5) to yield 0.24 g (18.7%) of 3 as a clear oil. TLC $R_f$=0.4 (EtOAc/Hexanes, 0.5:9.5)

Oxo-[2-(2-phenethyl-4-phenyl-butyryl)-piperidin-1-yl]-acetic acid methyl ester (5). To a solution of 0.24 g (0.55 mmol) of 3 in CH$_2$Cl$_2$ (2 mL) was added dropwise 0.13 mL (1.65 mmol) of trifluoroacetic acid, and the mixture was allowed to stir for 2 hours. The solution was diluted with CH$_2$Cl$_2$ (10 mL) and cooled to 0° C. followed by dropwise addition of 0.3 g (3.00 mmol) of triethylamine. After 5 minutes, to the solution was added dropwise 0.08 g (0.61 mmol) of chlorooxoacetate, and the mixture was stirred for 2 hours. The solution was quenched with H$_2$O and extracted with CH$_2$Cl$_2$ (2×200 mL). The organic phase was dried (MgSO$_4$) and evaporated to a clear oil which was subject to column chromatography (EtOAc/Hexanes, 1:3) to yield 0.19 g (81.9%) of 5 as a clear oil. TLC R$_f$=0.5 (EtOAc/Hexanes, 1:3)

3,3-Dimethyl-1-[2-(2-phenethyl-4-phenyl-butyryl)-piperidin-1-yl]-butane-1,2-dione (6). To a solution of 0.16 g (0.38 mmol) of 5 in anhydrous THF (2 mL) was added dropwise at −78° C. a 2.0M solution of 0.21 mL (0.42 mmol) of tert-butyl magnesium chloride in THF, and the mixture was stirred for 3 hours at −78° C. The solution was poured over saturated ammonium chloride (50 mL) and extracted with EtOAc (3×100 mL). The organic phase was dried (MgSO$_4$) and evaporated to a clear oil which was subject to column chromatography (EtOAc/Hexanes, 1:4) to yield 0.13 g (76.5%) of 6 as a clear oil. TLC R$_f$=0.62 (EtOAc/Hexanes, 1:4) $^1$H NMR (CDCl$_3$, 300 MHz): δ 1.40 (s, 9H); 1.36–2.29 (m, 9H); 2.62–2.82 (m, 4H); 3.39–3.52 (m, 2H); 5.18 (m, 1H); 5.31 (d, 1H, J=6.2); 5.42 (d, 1H, J=5.2); 7.42–7.26 (m, 10H); Anal. (C$_{29}$H$_{37}$NO$_3$) C, H, N.

3,3-Dimethyl-1-[2-(2-phenethyl-4-phenyl-butyryl)-piperidin-1-yl]-pentane-1,2-dione (7). To a solution of 0.38 g (0.90 mmol) of 5 in anhydrous THF (5 mL) was added dropwise at −78° C. a 1.0M solution of 1.9 mL (1.90 mmol) of 1,1-dimethylpropyl magnesium chloride in THF, and the mixture was stirred for 3 hours at −78° C. The solution was poured over saturated ammonium chloride (50 mL) and extracted with EtOAc (2×100 mL). The organic phase was dried (MgSO$_4$) and evaporated to a clear oil which was subject to column chromatography (EtOAc/Hexanes, 1:4) to yield 0.31 g (74.5%) of 6 as a clear oil. TLC R$_f$=0.8 (EtOAc/Hexanes, 1:4) $^1$H NMR (CDCl$_3$, 400 MHz): δ 0.94 (t, 3H, J=7.5 Hz); 1.24 (s, 3H); 1.28 (s, 3H); 1.42–2.06 (m, 11H); 2.36 (d, 1H, J=13.0 Hz); 2.61–2.89 (dt, 1H, J=3.2, 12.9 Hz); 3.42 (brt, 1H, J=12.8 Hz); 5.08 (ddd, 1H, J=5.2, 7.2,12.3); 5.32 (d, 1H, J=5.4 Hz); 7.16–7.32 (m, 10H); Anal. (C$_{30}$H$_{39}$NO$_3$) C, H, N.

Common Intermediates:

1,5-Diphenyl-pentan-3-ol (8a). To a solution of 12.8 g (95.2 mmol) of 3-phenyl-propionaldehyde in anhydrous THF (100 mL) was added dropwise at 0° C. a 1.0M solution of 100 mL (100 mmol) of phenethyl magnesium bromide in THF, and the mixture was stirred for 2 hours at 0° C. The solution was poured over saturated ammonium chloride and extracted with ether (3×150 mL). The organic phase was dried (MgSO$_4$) and evaporated to a solid, which was subject to column chromatography (EtOAc/Hexanes, 1:9) to yield 10.0 g (22.8%) of 8a as a white solid. TLC R$_f$=0.5 (EtOAc/Hexanes, 1:9)

3-Bromo-15-diphenylpentane (9a). To a solution of 2.29 g (95.3 mmol) of 8a and 3.48 g (10.48 mmol) of carbon tetrabromide in anhydrous CH$_2$Cl$_2$ (80 mL) was added portionwise at 0° C., 2.75 g (10.48 mmol) of triphenylphosphine, and the mixture was stirred for 1 hour at 0° C. followed by warming to an ambient temperature for 16 hours. The solution was evaporated and redissolved in EtOAc. White solid was filtered and the resulting solution was evaporated to an orange oil which was subject to column chromatography (EtOAc/Hexanes, 1:9) to yield 1.91 g (62.6%) of 9a as a clear oil. TLC R$_f$=0.8 (EtOAc/Hexanes, 1:9)

1,5-diphenylpentylmagnesium bromide (4a). A solution of 1.91 g (6.30 mmol) of 9a in anhydrous THF (10 mL) was added dropwise to 0.17 g (6.93 mmol) of magnesium powder stirred under an inert atmosphere for 16 hours. Upon complete addition, the solution was refluxed at 90° C. for 3 hours. The solution was cooled to an ambient temperature and used directly.

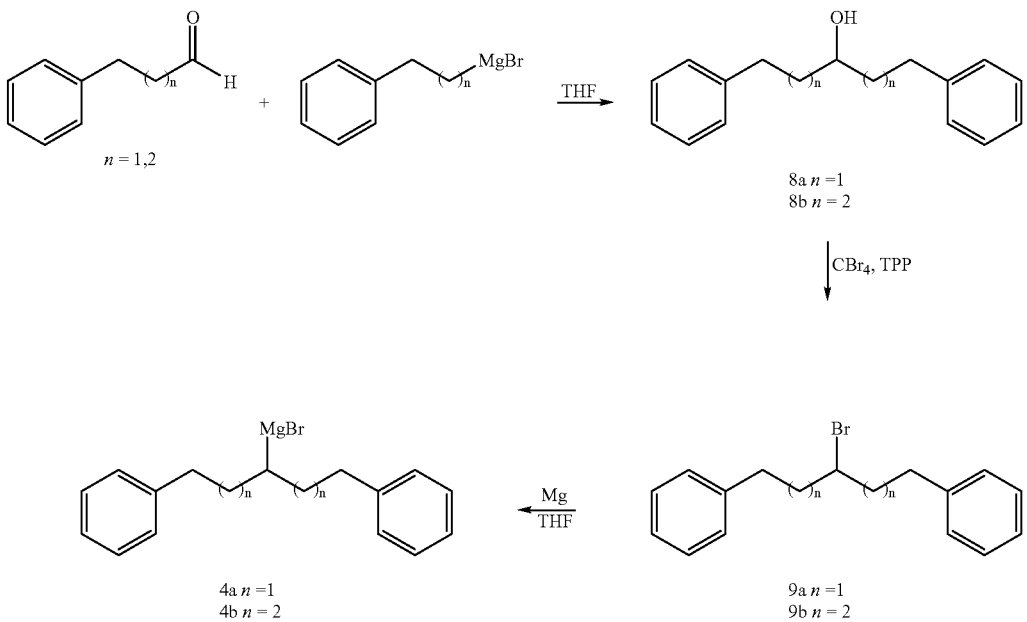

The following compounds were prepared by the method of Scheme VI.

Example 64

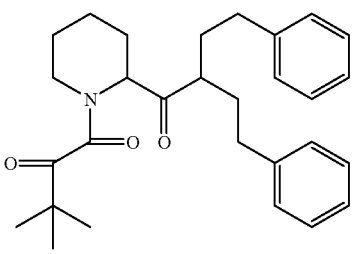

(2R,S)-2-({1-Oxo-[2-{2'-phenyl}ethyl]-4-phenyl}-butyl-1-(3,3-dimethyl-1,2-dioxobutyl)piperidine].

$^1$H NMR (CDCl$_3$, 300 MHz): δ 1.40 (s, 9H); 1.36–2.29 (m, 9H); 2.62–2.82 (m, 4H); 3.39–3.52 (m, 2H); 5.18 (m, 1H); 5.31 (d, 1H, J=6.2); 5.42 (d, 1H, J=5.2); 7.42–7.26 (m, 10H). Anal. Calcd. for C$_{29}$H$_{37}$NO$_3$·0.5 H2O: C, 76.28; H, 8.39; N, 3.07. Found: C, 76.02; H, 8.29; N, 2.99. TLC: R$_f$=0.62 (20% EtOAc/hexane). Physical form: Clear oil

Example 65

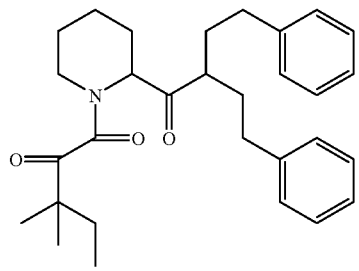

3,3-Dimethyl-1-[2-(2-phenethyl-4-phenylbutanoyl)piperidino]-1,2-pentanedione.

$^1$H NMR (CDCl$_3$, 400 MHz): δ 0.94 (t, 3H, J=7.5); 1.24,1.28 (s, 3H each); 1.42 –2.06 (m, 11H); 2.36 (d, 1H, J=13.0); 2.61–2.89 (dt, 1H, J=3.2, 12.9); 3.42 (br t, 1H, J=12.8); 5.08 (ddd, 1H, J=5.2, 7.2, 12.3); 5.32 (d, 1H, J=5.4); 7.16–7.32 (m, 10H). Anal. Calcd. for C$_{30}$H$_{39}$NO$_3$·0.7H2O: C, 75.98; H, 8.59; N, 2.95. Found: C, 75.72; H, 8.28; N, 2.95. TLC: R$_f$=0.8 (20% EtOAc:Hexane). Physical form: Clear oil

Example 66

Synthesis of Pyrrolidine Ketone Compounds

Scheme VII

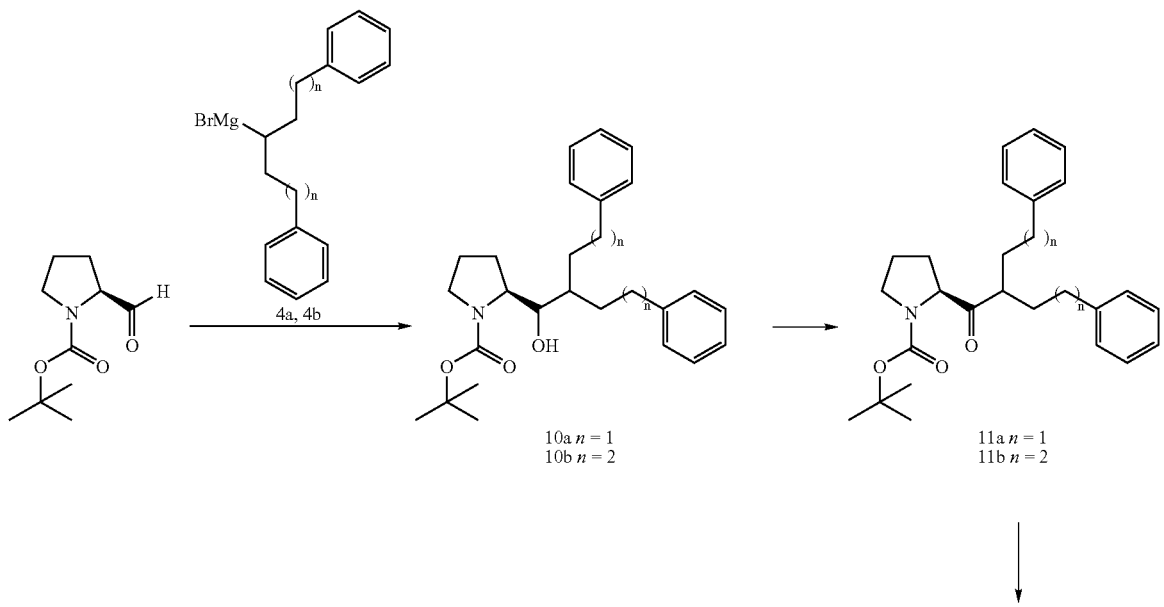

10a n = 1
10b n = 2

11a n = 1
11b n = 2

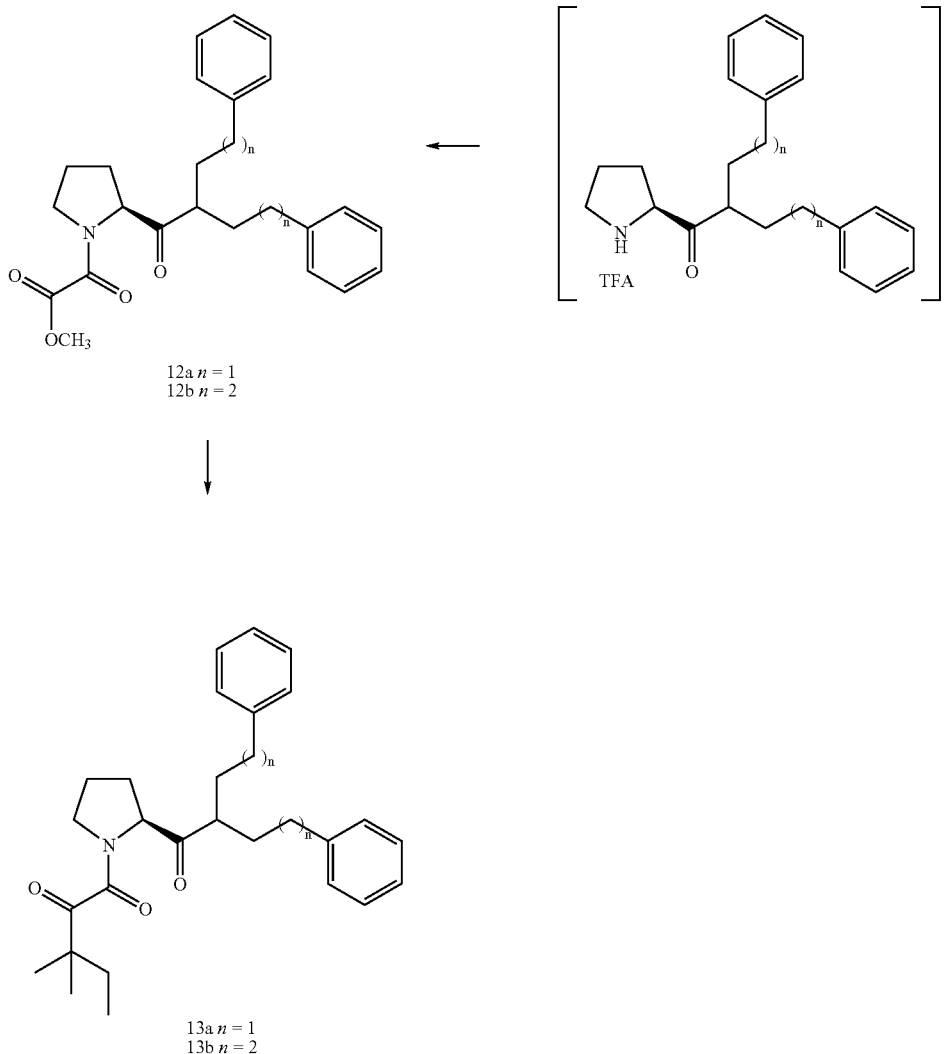

12a n = 1
12b n = 2

13a n = 1
13b n = 2

2-(1-Hydroxy-2-phenethyl-4-phenyl-butyl)-pyrrolidine-1-carboxylic acid tert-butyl ester (10a). To a solution of 0.5 g (2.5 mmol) of 2-formyl-pyrrolidine-1-carboxylic acid tert-butyl ester in anhydrous THF (20 mL) was added 5.0 mL (2.5 mmol) of 4a, and the mixture was stirred at an ambient temperature for 16 hours. The solution was poured over a 1N solution of hydrochloric acid and was extracted with EtOAc (2×100 mL). The organic phase was washed with saturated sodium bicarbonate, dried (MgSO$_4$) and evaporated to a clear oil which was subject to column chromatography (EtOAc/Hexanes, 1:3) to yield 0.18 g (16.7%) of 10a as a clear oil. TLC R$_f$=0.6 (EtOAc/Hexanes, 1:3)

2-(2-Phenethyl-4-phenyl-butyryl)-pyrrolidine-1-carboxylic acid tert-butyl ester (11a). To a solution of 0.22 g (1.0 mmol) of pyridinium chlorochromate in anhydrous CH$_2$Cl$_2$ (15 mL) was added dropwise a solution of 0.2 g (0.5 mmol) of 10a in anhydrous CH$_2$Cl$_2$ (5 mL), and the mixture was stirred at an ambient temperature for 16 hours. The solution was filtered and the resulting solution was evaporated to a yellow oil which was subject to column chromatography (EtOAc/Hexanes, 1:3) to yield 0.16 g (76.2%) of 11a as a clear oil. TLC R$_f$=0.5 (EtOAc/Hexanes, 1:3)

Oxo-[2-(2-phenethyl-4-phenyl-butyryl)-pyrrolidin-1-yl]-acetic acid methyl ester (12a). To a solution of 0.18 g (0.40 mmol) of 11a in CH$_2$Cl$_2$ (3 mL) was added dropwise 10 mL (8.77 mmol) of trifluoroacetic acid, and the mixture was allowed to stir for 2 hours. The solution was diluted with CH$_2$Cl$_2$ (10 mL) and cooled to 0° C. followed by dropwise addition of 0.7 g (10.00 mmol) of triethylamine. After 5 minutes, to the solution was added dropwise 0.06 g (0.5 mmol) of chlorooxoacetate, and the mixture was stirred for 2 hours. The solution was quenched with H$_2$O and extracted with CH$_2$Cl$_2$ (2×200 mL). The organic phase was dried (MgSO$_4$) and evaporated to a clear oil which was subject to column chromatography (EtOAc/Hexanes, 1:1) to yield 0.16 g (98.2%) of 12a as a clear oil. TLC R$_f$=0.6 (EtOAc/Hexanes, 1:3)

3,3-Dimethyl-1-[2-(2-phenethyl-4-phenyl-butyryl)-pyrrolidin-1-yl]-pentane-1,2-dione (13a). To a solution of 0.18 g (0.45 mmol) of 12a in anhydrous THF (2 mL) was added dropwise at −78° C. a 1.0M solution of 2.2 mL (2.20 mmol) of 1,1-dimethylpropyl magnesium chloride in THF, and the mixture was stirred for 3 hours at −78° C. The solution was poured over saturated ammonium chloride (50 mL) and extracted with EtOAc (3×100 mL). The organic phase was dried (MgSO$_4$) and evaporated to a clear oil which was subject to column chromatography (EtOAc/Hexanes, 1:3) to yield 0.14 g (76.5%) of 13a as a clear oil. TLC R$_f$=0.5 (EtOAc/Hexanes, 1:3) $^1$H NMR (CDCl$_3$, 400 MHz): δ 0.82–0.90 (m, 3H); 1.12–1.33 (m, 6H); 1.59–1.79 (m, 7H); 2.00–2.20 (m, 3H); 2.40–2.70 (t, 5H); 3.41–3.52 (m, 2H); 4.63–4.64 (m, 1H); 7.12–7.29 (m, 10H); Anal. (C$_{29}$H$_{37}$NO$_3$) C, H, N.

3,3-Dimethyl-1-{2-[5-phenyl-2-(3-phenyl-propyl)-pentanoyl]-pyrrolidin-1-yl}-pentane-1,2-dione (13b). To a solution of 0.12 g (0.28 mmol) of 12b in anhydrous THF (2 mL) was added dropwise at −78° C. a 1.0M solution of 0.3 mL (0.3 mmol) of 1,1-dimethylpropyl magnesium chloride in THF, and the mixture was stirred for 3 hours at −78° C. The solution was poured over saturated ammonium chloride (50 mL) and extracted with EtOAc (2×100 mL). The organic phase was dried (MgSO$_4$) and evaporated to a clear oil which was subject to column chromatography (EtOAc/Hexanes, 1:3) to yield 0.12 g (91.6%) of 13b as a clear oil. TLC R$_f$=0.6 (EtOAc/Hexanes, 1:3) $^1$H NMR (CDCl$_3$, 400 MHz): δ 0.89 (t, 3H, J=7.5 Hz); 1.23 (s, 3H); 1.28 (s, 3H); 1.34–2.11 (m, 15H); 2.58–2.83 (m, 4H); 3.43 (dt, 1H, J=6.4, 10.3 Hz); 3.56 (dt, 1H, J=7.1,10.3 Hz); 4.70 (dd, 1H, J=4.3 Hz); 7.12–7.31 (m, 10H); Anal. (C$_{31}$H$_{41}$NO$_3$) C, H, N.

The following compounds were prepared by the method of Scheme VII.

Example 67

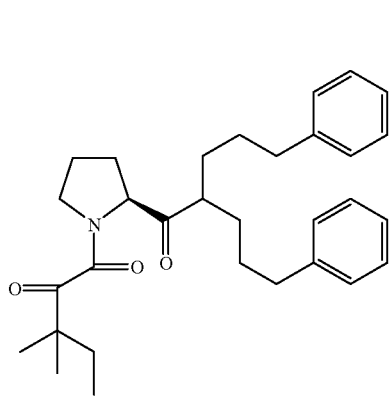

3,3-Dimethyl-1-{(2S)-2-[5-phenyl-1-(3-phenylpropyl) pentanoyl]-1-pyrrolidinyl}-1,2-pentanedione.

$^1$H NMR (CDCl$_3$, 400 MHz): δ 0.89 (t, 3H, J=7.5); 1.23 (s, 3H); 1.28 (s, 3H); 1.34–2.11 (m, 15H); 2.58–2.83 (m, 4H); 3.43 (dt, 1H, J=6.4, 10.3); 3.56 (dt, 1H, J=7.1, 10.3); 4.70 (dd, 1H, J=4.3); 7.12–7.31 (m, 10H). Anal. Calcd. for C$_{31}$H$_{41}$NO$_3$; C, 78.28; H, 8.69; N, 2.94. Found: C, 78.10; H, 8.75; N, 2.90. TLC: R$_f$=0.52 (25% EtOAc/hexane). Physical form: Colorless oil Example 68

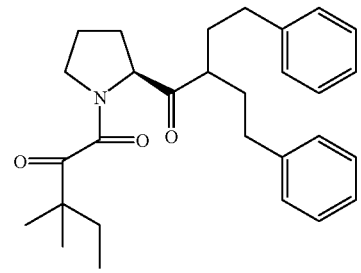

3,3-Dimethyl-1-{(2S)-2-[5-phenyl-1-(2-phenylethyl-4-phenylbutanoyl]-1-pyrrolidinyl}-1,2-pentanedione.

$^1$H NMR (CDCl$_3$, 400 MHz): δ 0.82–0.90 (m, 3H); 1.12–1.33 (m, 6H); 1.59–1.79 (m, 7H); 2.00–2.20 (m, 3H); 2.40–2.70 (t, 5H); 3.41–3.52 (m, 2H); 4.63–4.64 (m, 1H); 7.12–7.29 (m, 10H). Anal. Calcd. for C$_{29}$H$_{37}$NO$_3$·0.25 H$_2$O: C, 77.04; H, 8.36; N, 3.10. Found: C, 76.74; H, 8.25; N, 3.05.

Example 69

The general procedure for the synthesis of amide compounds is exemplified for Example 69, as follows:

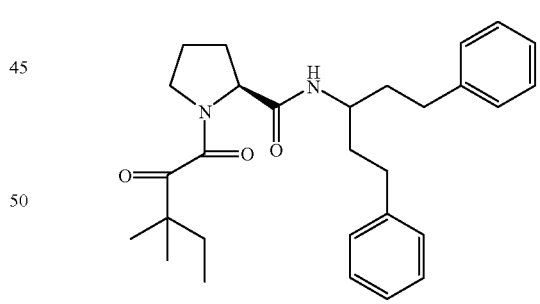

(2S)-[1-(3,3-Dimethyl-2-oxopentanoyl)pyrrolidin-2-yl]-N-(1-phenylethyl-3-phenylpropyl)formamide.

$^1$H NMR (CDCl$_3$, 400 MHz): δ 0.86 (t, 3H, J=7.5); 1.23 (s, 6H); 1.72 (m, 4H); 1.82 (m, 2H); 1.95 (m, 2H); 2.10 (m, 1H); 2.42 (m, 1H); 2.63 (m, 4H); 3.47 (m, 2H); 4.02 (m, 1H); 4.56 (m, 1H); 6.58 (m, 1H); 7.21 (m, 10H). Anal. Calcd. for C$_{29}$H$_{38}$N$_2$O$_3$·H$_2$O: C, 72.47; H, 8.39; N, 5.83. Found: C, 72.09; H, 7.91; N, 5.71. TLC: R$_f$=0.70 (50% EtOAc/hexane). Physical form: Oil Scheme VIII

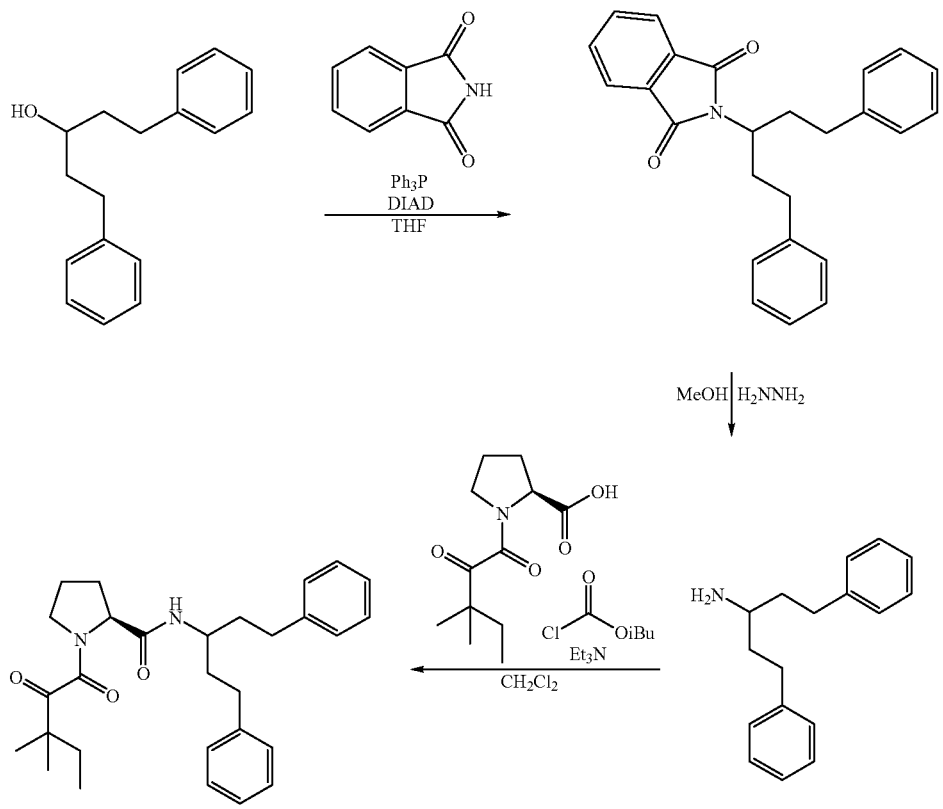

10564-103 2-(1-Phenyl-3-phenyl-propyl)-isoindole-1,3-dione. To a solution of 1,5-diphenyl-3-pentanol (0.65 g, 2.7 mmol), phthalimide (0.40 g, 2.7 mmol) and triphenylphosphine (0.75 g, 2.8 mmol) in 17 mL THF was added dropwise DIAD (0.55 g, 0.27 mmol) and the mixture stirred 1d. The mixture was then concentrated and the product purified on silica gel using 9:1 hexane:ethyl acetate to a clear oil: 0.70 g (70%); 1H NMR (CDCl3, 400 MHz): δ 1.98–2.07(m, 2H); 2.47–2.63(m, 6H); 4.28–4.35(m, 1H); 7.03–7.26(m, 10H); 7.66–7.78(m, 4H). TLC: $R_f$=0.60 (EtOAc:Hexane 1:4)

10564-105 1,5-Diphenyl-3-pentylamine. To a solution of 10564-103 (0.68 g, 1.8 mmol) in 20 mL methanol was added hydrazine monhydrate (0.92 g, 18 mmol) and the mixture heated at reflux temperature for 3 h. The mixture was cooled to 4° C. and filtered. The filtrate was concentrated to yield product as a clear oil: 0.39 g (89%); 1H NMR (CDCl3, 400 MHz): δ 1.53–1.66(m, 2H); 1.71–1.84(m, 2H); 2.43–2.92 (m, 7H); 7.12–7.32(m, 10H).

10564-111 1-(3,3-Dimethyl-2-oxo-pentanoyl)-pyrrolidine-2-carboxylic acid (1-phenethyl-3-phenyl-propyl)-amide. To a solution of 1-(3,3-Dimethyl-2-oxo-pentanoyl)-pyrrolidine-2-carboxylic acid (0.44 g, 1.8 mmol) and triethylamine (0.19 g, 1.8 mmol) in 7 mL dichloromethane under argon and cooled in an ice bath was added dropwise isobutyl chloroformate and the mixture stirred 5 min. At this time, a solution of 10564-105 (0.40 g, 1.7 mmol) was added dropwise and the mixture stirred 1.5 h. allowing it to warm to r.t. The mixture was then concentrated and the product purified on silica gel using 3:1 hexane ethyl acetate to a clear oil: 0.45 g (58%); 1H NMR (CDCl3, 400 MHz): δ 0.86(t, J=7.5 Hz, 3H); 1.21(s, 6H); 1.51–1.57(m, 2H); 1.67–2.16(m, 8H); 2.40–2.73(m, 4H); 3.41–3.52(m, 2H); 3.97–4.05(m, 1H); 3.52–3.58(m, 1H); 6.58(d, J=7.2 Hz, 1H); 7.10–7.32 (m, 10H). Anal. Calc'd for $C_{29}H_{38}N_2O_3$: C, 72.47; H, 8.39; N, 5.83. Found: C, 72.09; H, 7.94; N, 5.71. TLC: $R_f$=0.70 (EtOAc:Hexane 1:1)

Example 70

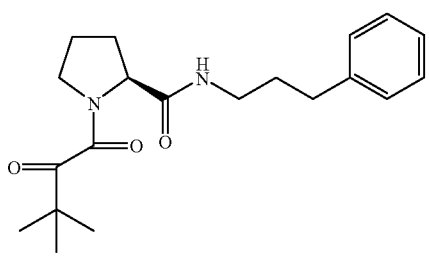

(2S)-[1-(3,3-Dimethyl-2-oxobutanoyl)pyrrolidin-2-yl]-N-(3-phenylpropyl)formamide.

1H NMR (CDCl3, 400 MHz): δ 1.27 (s, 9H); 1.83 (m, 2H); 1.93 (m, 2H); 2.08 (m, 1H); 2.45 (m, 2H); 2.66 (m, 2H); 3.28 (m, 2H); 3.42 (m, 2H); 4.54 (m, 1H); 5.82 (m, 1H); 7.26 (m, 5H). Anal. Calcd. for $C_{20}H_{28}N_2O_3$: C, 69.74; H, 8.19; N, 8.13. Found: C, 68.74; H, 8.18; N, 7.91. TLC: $R_f$=0.40 (50% EtOAc/hexane). Physical form: Oil

Example 71

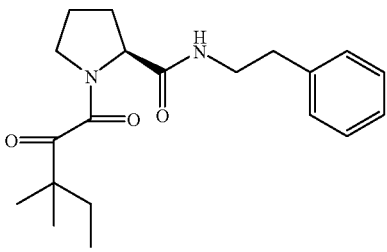

(2S)-[1-(3,3-Dimethyl-2-oxopentanoyl)pyrrolidin-2-yl]-N-(2-phenethyl) formamide $^1$H NMR (CDCl$_3$, 400 MHz): δ 0.83 (t, 3H, J=7.5); 1.20 (s, 6H); 1.69 (m, 2H); 1.95 (m, 1H); 2.28 (m, 1H); 2.80 (m, 2H); 3.38 (m, 2H); 3.50 (m, 2H); 4.42 (m, 1H); 6.75 (br, 1H); 7.22–7.29 (m, 5H). Anal. Calcd. for C$_{20}$H$_{28}$N$_2$O$_3$: C, 69.74; H, 8.19; N, 8.13. Found: C, 69.49; H, 8.13; N, 8.13. TLC: R$_f$=0.50 (33% EtOAc/hexane). Physical form: Oil.

Example 72

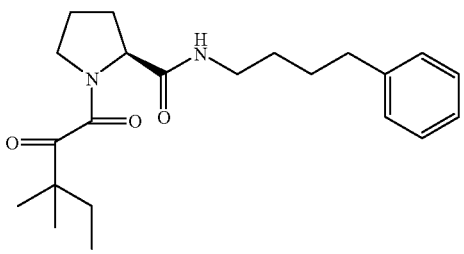

(2S)-[1-(3,3-Dimethyl-2-oxopentanoyl)pyrrolidin-2-yl]-N-(4-phenylbutyl)formamide.

$^1$H NMR (CDCl$_3$, 400 MHz): δ 0.86 (t, 3H, J=7.5); 1.21 (s, 6H); 1.53–1.71 (m, 6H); 1.90 (m, 2H); 2.05 (m, 1H); 2.41 (m, 1H); 2.60 (m, 2H); 3.26 (m, 2H); 3.43 (m, 2H); 4.54 (m, 1H); 6.85 (br, 1H); 7.25–7.28 (m, 5H). Anal. Calcd. for C$_{22}$H$_{32}$N$_2$O$_3$; C, 70.94; H, 8.66; N, 7.52. Found: C, 70.79; H, 8.58; N, 7.42. TLC: R$_f$=0.50 (33% EtOAc/hexane). Physical form

Example 73

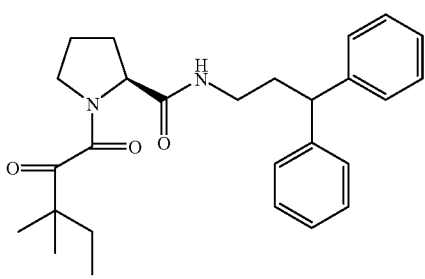

(2S)-[1-(3,3-Dimethyl-2-oxopentanoyl)pyrrolidin-2-yl]-N-(3,3-diphenylpropyl)formamide.

$^1$H NMR (CDCl$_3$, 400 MHz): δ 0.88 (t, 3H, J=7.5); 1.21 (s, 6H); 1.69 (m, 2H); 1.88 (m, 2H); 2.08 (m, 1H); 2.25 (m, 2H); 2.30 (m, 1H); 3.20 (m, 2H); 3.41 (m, 2H); 3.97 (m, 1H); 4.50 (m, 1H); 7.20–7.28 (m, 10H). Anal. Calcd. for C$_{27}$H$_{34}$N$_2$O$_3$: C, 74.62; H, 7.89; N, 6.45. Found: C, 74.57; H, 7.85; N, 6.43. TLC: R$_f$=0.35 (25% EtOAc/hexane). Physical form: Oil.

Example 74

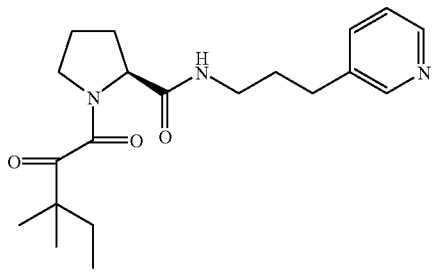

(2S)-[1-(3,3-Dimethyl-2-oxopentanoyl)pyrrolidin-2-yl]-N-(3-(3-pyridyl)propyl)formamide.

$^1$H NMR (CDCl$_3$, 400 MHz): δ 0.86 (t, 3H, J=7.5); 1.22 (s, 6H); 1.71 (m, 2H); 1.83 (m, 2H); 1.94 (m, 2H); 2.02 (m, 1H); 2.35 (m, 1H); 2.62 (m, 2H); 3.28 (m, 2H); 3.46 (m, 2H); 4.56 (m, 1H); 7.10 (m, 1H); 7.50 (m, 1H); 8.44 (m, 2H). Anal. Calcd. for C$_{20}$H$_{29}$N$_3$O$_3$·0.5 H$_2$O: C, 65.19; H, 8.21; N, 11.40. Found: C, 64.47; H, 8.01; N, 11.94. TLC: R$_f$=0.45 (25% EtOAc/hexane). Physical form: Oil.

Example 75

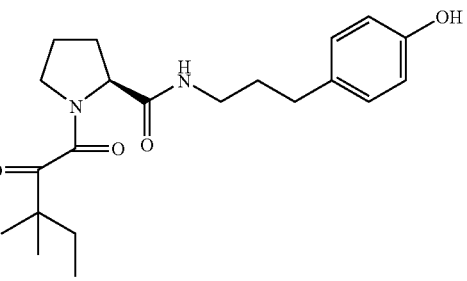

(2S)-[1-(3,3-Dimethyl-2-oxopentanoyl)pyrrolidin-2-yl]-N-[3-(4-hydroxyphenyl)propyl]formamide.

$^1$H NMR (CDCl$_3$, 400 MHz): δ 0.88 (t, 3H, J=7.5); 1.24 (s, 6H); 1.70 (m, 6H); 1.78 (m, 2H); 2.05 (m, 1H); 2.41 (m, 1H); 2.54 (t, 2H); 3.24 (m, 2H); 3.44 (m, 2H); 4.53 (m, 1H); 6.73 (d, 2H, J=8.30); 6.75 (br, 1H); 6.98 (d, 2H, J=8.30). Anal. Calcd. for C$_{21}$H$_{30}$N$_2$O$_4$·0.5 H$_2$O: C, 65.77; H, 8.15; N, 7.30. Found: C, 65.63; H, 7.90; N, 7.05. TLC: R$_f$=0.45 (50% EtOAc/hexane). Physical form: Thick oil.

Example 76

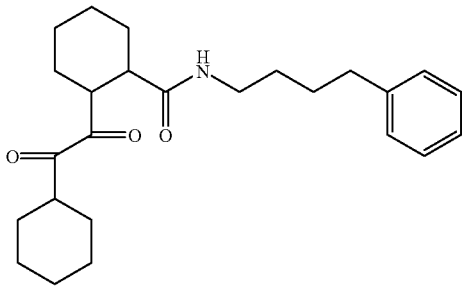

N2-(4-Phenylbutyl)-N-(2-oxo-2-phenylacetyl)-2-piperidinecarboxamide.

$^1$H NMR (CDCl$_3$, 300 MHz): δ 1.25–1.80 (m, 7H); 2.32–2.80 (m, 3H); 3.10–3.50 (m, 5H); 4.06 (m, 1H); 5.24 (m, 1H); 6.03 (m, 1H); 7.15–7.32 (m, 5H); 7.45–7.60 (m, 2H); 7.65–7.80 (m, 1H); 8.00–8.10 (m, 2H). Anal.Calcd. for C$_{24}$H$_{27}$N$_2$O$_3$·0.5 H$_2$O: C, 71.98; H, 7.05; N, 6.99. Found: C, 71.95; H, 7.06; N, 7.12. TLC: R$_f$=0.20 (2:1 hexane:EtOAc) Physical form: Clear oil

Example 77

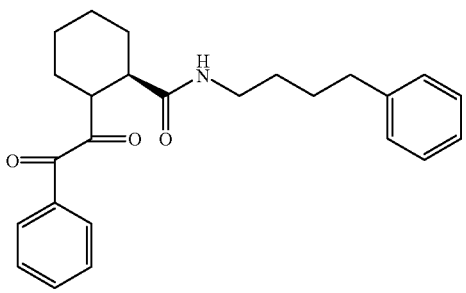

(2S)-1[-(2-oxo-2-phenylacetyl)(2-piperidyl)]-N-(4-phenylbutyl)-formamide.

$^1$H NMR (CDCl$_3$, 400 MHz): δ 1.64–1.85 (m, 10H); 2.05 (m, 1H); 2.38 (m, 3H); 3.31 (m, 2H); 3.45 (m, 1H); 4.05 (m, 1H); 5.22 (m, 1H); 6.08 (br, 1H); 6.55 (br, 1H); 7.25–7.97 (m, 10H). Anal. Calcd. for C$_{24}$H$_{28}$N$_2$O$_3$·0.7 H2O: C, 71.16; H, 7.31; N, 6.92. Found: C, 71.25; H, 7.14; N, 6.92. TLC: R$_f$=0.60 (1:1 Hexane/EtOAc). Physical form: Oil

Example 78

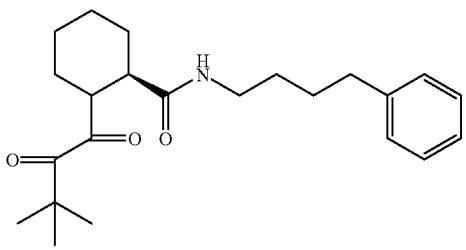

(2S)-[1-(3,3-Dimethyl-2-oxobutanoyl)(2-piperidyl)]-N-(4-phenylbutyl)formamide.

$^1$H NMR (CDCl$_3$, 400 MHz): δ 1.27 (s, 9H); 1.69–1.82 (m, 10H); 2.30–2.62 (m, 4H); 2.43 (m, 1H); 2.50 (m, 2H); 3.80 (m, 1H); 4.72 (m, 1H); 5.95 (br, 1H); 6.60 (br, 1H); 7.20–7.56 (m, 5H). Anal. Calcd. for C$_{22}$H$_{32}$N$_2$O$_3$: C, 70.94; H, 8.66; N, 7.52. Found: C, 70.67, 8.63; N, 7.25. TLC: R$_f$=0.75 (1:1 Hexane/EtOAc). Physical form: Oil

Example 79

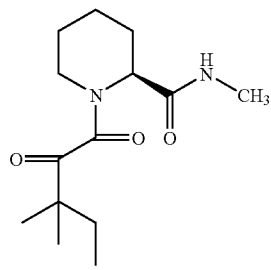

(2S)-[1-(3,3-Dimethyl-2-oxopentanoyl)(2-piperidyl)]-N-methylformamide.

$^1$H NMR (CDCl$_3$, 400 MHz): δ 0.90(t, 3H, J=7.5); 1.22(s, 6H); 1.45(m, 2H); 1.72(m, 4H); 2.47(m, 2H); 2.83(m, 3H); 3.25(m, 2H); 5.08(m, 1H). Anal. Calcd. for: C, 61.10; H, 9.07; N, 10.18. Found: C, 61.12; H, 8.84; N, 10.01. TLC: R$_f$ 0.40; 1:1 hexane:EtOAc. Physical form: clear oil.

Example 80

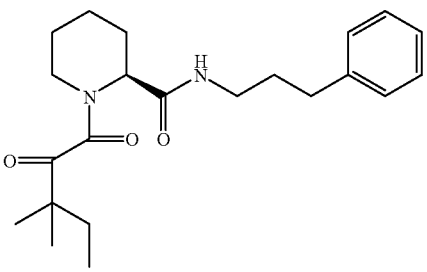

(2S)-[1-(3,3-Dimethyl-2-oxopentanoyl)(2-piperidyl)]-N-(3-phenylpropyl)formamide.

$^1$H NMR (CDCl$_3$, 400 MHz): δ 0.90(t, 3H, J=7.5); 1.22(s, 6H); 1.45(m, 2H); 1.72(m, 4H); 1.83(m, 2H); 2.45(m, 2H); 2.65(m, 2H); 3.20(m, 2H); 3.30(m, 2H); 5.08(m, 1H); 6.02 (bs, 1H); 7.23(m, 5H). Anal. Calcd. for: C, 70.26; H, 8.68; N, 7.45. Found: C, 70.11; H, 8.67; N, 7.46. TLC: R$_f$ 0.73; 1:1 hexane:EtOAc. Physical form: white solid.

Example 81

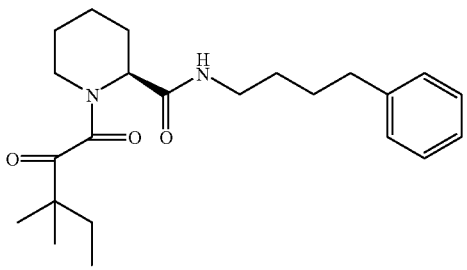

¹H NMR (CDCl₃, 400 MHz): δ 0.90(t, 3H, J=7.5); 1.22(s, 6H); 1.54(m, 4H); 1.71(m, 6H); 2.45(m, 2H); 2.63(m, 2H); 3.20(m, 2H); 3.30(m, 2H); 5.04(m, 1H); 6.00(bs, 1H); 7.23(m, 5H) Anal. Calcd. for: C, 70.39; H, 8.90; N, 7.14. Found: C, 70.38; H, 8.78; N, 7.11. TLC: $R_f$ 0.77; 1:1 hexane:EtOAc. Physical form: clear oil.

Example 82

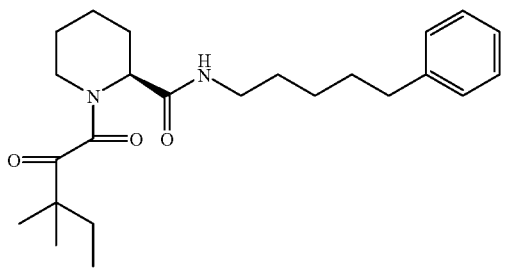

(2S)-[1-(3,3-Dimethyl-2-oxopentanoyl)(2-piperidyl)]-N-(5-phenylpentyl)formamide.

¹H NMR (CDCl₃, 400 MHz): δ 0.90(t, 3H, J=7.5); 1.23(s, 6H); 1.40(m, 2H); 1.52(m, 4H); 1.71(m, 6H); 2.45(m, 2H); 2.61(m, 2H); 3.15(m, 2H); 3.28(m, 2H); 5.05(d, 1H, J=5.4); 5.96(bs, 1H); 7.21(m, 5H). Anal. Calcd. for: C, 71.96; H, 9.06; N, 6.99 Found: C, 71.94; H, 9.10; N, 6.94. TLC: $R_f$ 0.47; 2:1 hexane:EtOAc. Physical form: clear oil.

Example 83

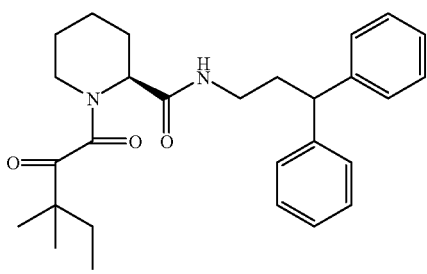

(2S)-[1-(3,3-Dimethyl-2-oxopentanoyl)piperidin-2-yl]-N-(3,3-diphenylpropyl)formamide.

¹H NMR (CDCl₃, 400 MHz): δ 0.91(t, 3H, J 7.5); 1.23(s, 6H); 1.72(m, 6H); 2.28(m, 3H); 3.20(m, 3H); 4.00(m, 3H); 5.02(m, 1H); 5.98(bs, 1H); 7.24(m, 10H); Anal. Calcd. for: C, 73.83; H, 8.15; N, 5.90. Found: C, 73.83; H, 8.10; N, 5.77. TLC: $R_f$ 0.62; 2:1 hexane:EtOAc. Physical form: clear oil.

Example 84

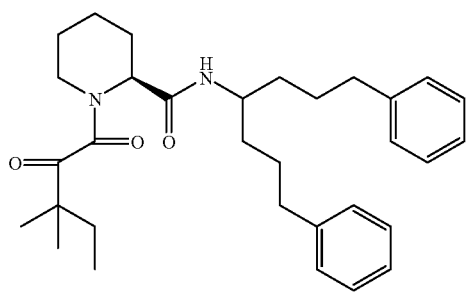

(2S)-[1-(3,3-Dimethyl-2-oxopentanoyl)piperidin-2-yl]-N-(1,7-diphenyl-4-heptyl)formamide.

¹H NMR (CDCl₃, 400 MHz): δ 0.90(t, 3H, J=7.5); 1.23(m, 6H); 1.60(m, 14H); 2.40(m, 1H); 2.61(m, 3H); 3.17(m, 1H); 4.00(m, 2H); 5.05(m, 1H); 5.68(m, 1H); 7.25(m, 10H). Anal. Calcd. for: C, 76.15; H, 8.79; N, 5.55. Found: C, 76.22; H, 8.82; N, 5.50. TLC: $R_f$ 0.82; 2:1 hexane:EtOAc. Physical form: clear oil.

Example 85

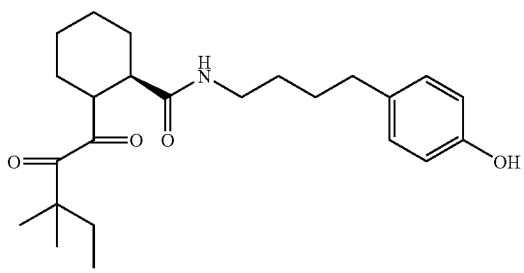

(2S)-[1-(3,3-Dimethyl-2-oxopentanoyl)(2-piperidyl)]-N-(4-{parahydroxyphenyl}butyl)formamide.

¹H NMR (CDCl₃, 400 MHz): δ 0.90(t, 3H, J=7.5); 1.26(m, 8H); 1.50(m, 4H); 1.70(m, 4H); 2.55(m, 2H); 3.20(m, 3H); 4.13(m, 1H); 4.98(m, 2H); 5.05(m, 1H); 6.34(bs, 1H); 6.90(m, 4H). Anal. Calcd. for: C, 68.63; H, 8.51; N, 6.96. Found: C, 68.57; H, 8.51; N, 6.90. TLC: $R_f$ 0.23; 2:1 hexane:EtOAc. Physical form: clear oil.

Example 86

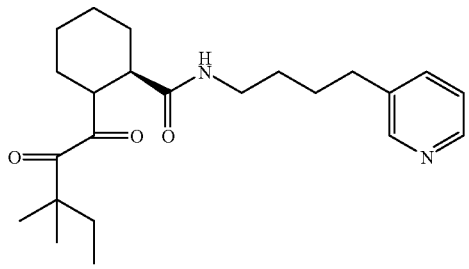

(2S)-[1-(3,3-Dimethyl-2-oxopentanoyl)(2-piperidyl)]-N-(4-{3-pyridyl}butyl)formamide.

$^1$H NMR (CDCl$_3$, 400 MHz): δ 0.90(t, 3H, J=7.5); 1.22(m, 6H); 1.62(m, 12H); 2.45(m, 2H); 3.10(m, 1H); 3.32(m, 3H); 5.05(d, 1H, J=5.3); 6.05(bs, 1H); 7.21(m, 1H); 7.51(m, 1H); 8.43(m, 2H). Anal. Calcd. for: C, 67.40; H, 8.61; N, 10.72. Found: C, 67.49; H, 8.61; N, 10.68. TLC: R$_f$ 0.18; 100% EtOAc. Physical form: clear oil

Example 87

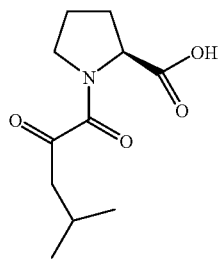

(2S)-1-(4-Methyl-2-oxopentanoyl)pyrrolidine-2-carboxylic acid.

$^1$H NMR (CDCl$_3$, 400 MHz): δ 0.88–0.97 (m, 6H); 1.82–2.18 (m, 5H); 2.70–2.83 (m, 2H); 3.78 (m, 2H); 4.90 (m,1H); 7.98 (br,1H). Anal. Calcd. for C$_{11}$H$_{17}$NO$_4$-0.25 H$_2$O: C, 57.01; H, 7.61; N, 6.01. Found: C, 57.30; H, 7.57; N, 5.91. Physical form: Semisolid.

Example 88

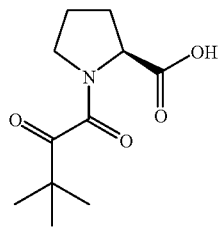

(2S)-1-(1,2-dioxo-3,3-dimethylbutyl)-2-pyrrolidinecarboxylic acid.

$^1$H NMR (CDCl$_3$, 400 MHz): □1.28 (s, 9H); 1.95–2.06 (m, 2H); 2.17–2.26 (m, 2H); 3.48–3.52 (m, 2H); 4.52 (d, 1H); 7.95 (br, 1H). Anal. Calcd. for C$_{11}$H$_{17}$NO$_4$: C, 58.14; H, 7.54; N, 6.16. Found: C, 58.40; H, 7.56; N, 6.14. Physical form: White solid.

Example 89

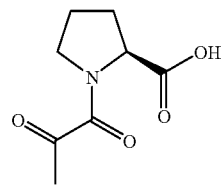

1-(2-oxopropanoyl)pyrrolidine-2-carboxylic acid.

$^1$H NMR (CDCl$_3$, 400 MHz): δ 1.98–2.10 (m, 1H); 2.21–2.30 (m, 1H); 2.41 (s, 3H); 3.66 (m, 2H); 3.77 (m, 2H); 4.87 (m, 1H); 10.46 (s, 1H). Anal. Calcd for C$_8$H$_{11}$NO$_4$-0.1 H$_2$O: C: 51.39; H: 6.04; N: 7.49; found: C: 51.41; H: 6.27; N: 7.10. Physical form: yellow gum.

Example 90

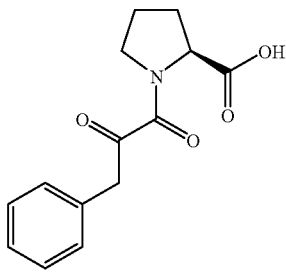

(2S)-1-(2-Oxo-3-phenylpropanoyl)pyrrolidine-2-carboxylic acid.

$^1$H NMR (CDCl$_3$, 400 MHz): δ 1.86–2.26 (m, 4H); 3.59 (m, 2H); 4.06–4.16 (m, 2H); 4.50 (m, 1H); 7.18–7.33 (m, 5H); 8.12 (br, 1H). Anal. Calcd. for C$_{14}$H$_{15}$NO$_4$-0.25 H$_2$O: C, 63.27; H, 5.88; N, 5.27. Found: C, 63.33; H, 6.09; N, 4.49. Physical form: Yellow oil.

Example 91

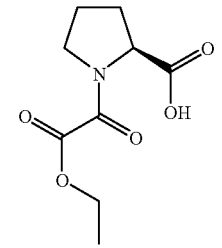

L-[1-(2,3-dioxo-4-oxapentyl)]proline.

$^1$H NMR (CDCl$_3$, 400 MHz): δ 1.31–1.40 (m, 3H); 1.87–2.49 (m, 4H); 3.61–3.87 (m, 2H); 4.23–4.36 (m, 2H); 4.58 and 4.93 (two sets of dd's of both rotamers, 1H); 9.62

(br.s, 1H). Anal. Calcd for $C_9H_{13}N_1O_5$: C, 50.23; H, 6.09; N, 6.51. Found: C, 50.11; H, 6.38; N, 6.04. Physical form: Yellow oil.

Example 92

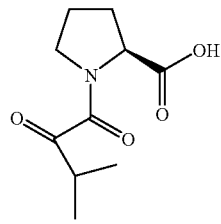

1-(3-methyl-2-oxobutanoyl)pyrrolidine-2-carboxylic acid $^1$H NMR (CDCl$_3$, 400 MHz): δ 1.05–1.20 (m, 6H); 1.93–2.53 (m, 5H); 3.53–3.76 (m, 2H); 4.17–4.19 (m, 1H); 7.80(br s, 1H). Anal. Calcd for $C_{10}H_{15}NO_4$-0.05 mol H$_2$O: C: 56.09; H: 7.11; N: 6.54; found: C: 55.91; H: 7.16; N: 6.36. Physical form: oil

Example 93

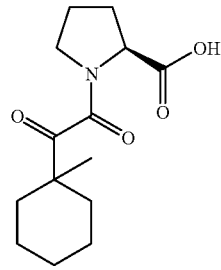

(2S)-1-[2-(Methylcyclohexyl)-2-oxoacetyl]pyrrolidine-2-carboxylic acid.

$^1$H NMR (CDCl$_3$, 400 MHz): δ 1.29 (s, 3H); 1.30–1.40 (m, 6H); 1.54–1.56 (m, 4H); 1.95–2.11 (m, 4H); 3.52–3.59 (m, 2H); 4.54 (dd, 1H, J=4,5); 10.30 (br s, 1H). Anal. Calcd for $C_{14}H_{21}N_1O_4$: C: 62.90; H: 7.92; N: 5.24; found: C: 61.29; H: 7.75; N: 5.02. Physical form: optically pure white solid

Example 94

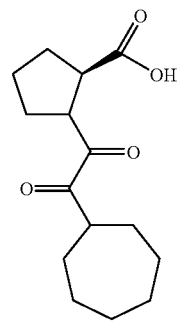

(2S)-1-(2-cycloheptyl-2-oxoacetyl)pyrrolidine-2-carboxylic acid.

$^1$H NMR (CDCl$_3$, 400 MHz): δ 1.27–1.41 (m, 10H); 1.51–1.98 (m, 4H); 2.00–2.17 (m, 1H); 3.12–3.17 (m, 1H); 3.30–3.44 (m, 2H); 4.44 (dd, 1H, J=4,5). Anal. Calcd for $C_{14}H_{21}NO_4$: C: 62.90; H: 7.92; N: 5.24 found: C: 62.74; H: 7.83; N: 5.11. Physical form optically pure white solid.

Example 95

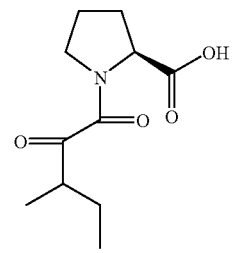

1-(3-methyl-2-oxopentanoyl)pyrrolidine-2-carboxylic acid.

NMR: $^1$H NMR (CDCl3, 400 MHz) 0.88–0.96 (m, 3H); 1.06–1.14 (m, 3H); 1.25–1.50 (m, 1H); 1.67–2.11 (m, 3H); 2.19–2.24 (m, 2H); 3.20–3.30 (m, 1H); 3.60–3.78 (m, 2H); 4.59 (t, 1H, J=6.0); 9.47 (bs, 1H). TLC: $R_f$=0.36 (5% MeOH/EtOAc/5 drops HOAc). Anal: Calcd for: C, 58.14; H, 7.54; N, 6.16. Found: C, 58.32; H, 7.71; N, 6.04. Physical Form: Clear oil The invention being thus described, it will be obvious that the same may be varied in many ways. Such variations are not to be regarded as a departure from the spirit and scope of the invention and all such modification are intended to be included within the scope of the following claims.

---

We claim:

1. A method for stimulating neurite outgrowth by a nerve cell, comprising:

administering to said nerve cell an effective amount of compound having an affinity for FKBP-type immunophilins according to formula I

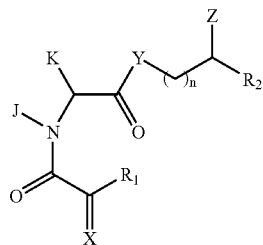

Formula I or a pharmaceutically acceptable salt thereof, wherein Y is $CH_2$, O, NH, or N—(C1–C4 alkyl);

wherein Z and $R_2$ are independently Ar, (C5–C7)-cycloalkyl substituted (C1–C6)-straight or branched alkyl or alkenyl, (C5–C7)-cycloalkenyl substituted (C1–C6)-straight or branched alkyl or alkenyl, or Ar substituted (C1–C6)-straight or branched alkyl or alkenyl, wherein in each case, one or two carbon atoms of the straight or branched alkyl or alkenyl groups may be substituted with 1–2 heteroatoms selected from the group consisting of oxygen, sulfur, SO and $SO_2$ in chemically reasonable substitution patterns, or

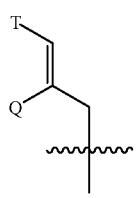

wherein Q is hydrogen, (C1–C6)-straight or branched alkyl or (C1–C6)-straight or branched alkenyl;

wherein T is Ar or substituted 5–7 membered cycloalkyl with substituents at positions 3 and 4 which are independently selected from the group consisting of hydrogen, hydroxyl, O—(C1–C4)-alkyl or O—(C1–C4)-alkenyl and carbonyl;

wherein Ar is selected from the group consisting of monocyclic and bicyclic heterocyclic aromatic ring systems with individual ring sizes being 5 or 6 which may contain in either or both rings a total of 1–4 hetero atoms independently selected from oxygen, nitrogen and sulfur;

wherein Ar may contain one to three substituents which are independently selected from the group consisting of hydrogen, halo, hydroxyl, hydroxymethyl, nitro, $CF_3$, trifluoromethoxy, (C1–C6)-straight or branched alkyl or (C1–C6)-straight or branched alkenyl, O-(C1–C4)-straight or branched alkyl or O—(C1–C4)-straight or branched alkenyl, O-benzyl, O-phenyl, amino, 1,2-methylenedioxy, carbonyl and phenyl;

wherein $R_1$ is either hydrogen or U; X is either oxygen or CH—U, provided that if $R_1$ is hydrogen, then X is CH—U, or if X is oxygen then $R_1$ is U;

wherein U is hydrogen, O—(C1–C4)-straight or branched alkyl or O—(C1–C4)-straight or branched alkenyl, (C1-C6)-straight or branched alkyl or (C1-C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C1–C4)-alkyl or (C1–C4)-alkenyl]-Ar or Ar (Ar as described above);

wherein J is hydrogen or C1 or C2 alkyl or benzyl; K is (C1–C4)-straight or branched alkyl, benzyl or cyclohexylethyl; or wherein J and K may be taken together to form a 5 membered heterocyclic ring which may contain an oxygen (O), sulfur (S), SO or $SO_2$ substituted therein; and wherein n is 0–3.

2. The method of claim 1, further comprising co-administering an effective amount of a neurotrophic factor to stimulating neurite outgrowth selected from the group consisting of nerve growth factor, brain derived growth factor, glial derived growth factor, and neurotropin-3.

3. The method of claim 1, wherein Z and $R_2$ are independently Ar, (C5–C7)-cycloalkyl substituted (C1–C6)-straight or branched alkyl or alkenyl, (C5–C7)-cycloalkenyl substituted (C1–C6)-straight or branched alkyl or alkenyl, or Ar substituted (C1–C6)-straight or branched alkyl or alkenyl, wherein in each case, one or two carbon atoms of the straight or branched alkyl or alkenyl groups may be substituted with 1–2 heteroatoms selected from the group consisting of oxygen, sulfur, SO and $SO_2$ in chemically reasonable substitution patterns;

wherein U is hydrogen, O—(C1–C4)-straight or branched alkyl or O—(C1–C4)-straight or branched alkenyl, (C1–C6)-straight or branched alkyl or (C1–C6)-straight or branched alkenyl, (C5–C7)-cycloalkenyl substituted with (C1–C4)-straight or branched alkyl or (C1–C4)-straight or branched alkenyl, [(C1–C4)-alkyl or (C1–C4)-alkenyl]-Ar or Ar; and wherein Ar is selected from the group consisting of monocyclic and bicyclic heterocyclic aromatic ring systems with individual ring sizes being 5 or 6, which may contain in either or both rings a total of 1–4 heteroatoms independently selected from oxygen, nitrogen and sulfur;

wherein Ar may contain one to three substituents which are independently selected from the group consisting of hydrogen, halo, hydroxyl, hydroxymethyl, intro, $CF_3$, tnfluoromethoxy, (C1–C6)-straight or branched alkyl or (C1–C6)-straight or branched alkenyl, O—(C1–C4)-straight or branched alkyl or O—(C1–C4)-straight or branched alkenyl, O-benzyl, O-phenyl, amino, and 1,2-methylenedioxy.

4. The method of claim 3, wherein if X is O, Y is O, NH or N—(C1–C4 alkyl), $R_1$ is C1–C6 straight or branched alkyl, C2–C6 straight or branched alkenyl, C5–C7 cycloalkyl or cycloalkenyl substituted with C1–C4 straight or branched alkyl or C2–C4 straight or branched alkenyl, and Ar is 1-napthyl, 2-napthyl, indolyl, 2-furyl, 3-furyl, 2-thienyl, 3-thienyl, 2-pyridyl, 3-pyridyl, 4-pyridyl, or phenyl then $(CH_2)_nZ$ and $R_2$ taken together do not form:

1) substituted or unsubstituted indolyl, 2-furyl, 3-furyl, thiazolyl, 2-thienyl, 3-thienyl, 2-pyridyl, 3-pyridyl, 4-pyridyl, phenyl 2) an alkyl or alkenyl chain with substituted or unsubstituted indolyl, 2-furyl, 3-furyl, thiazolyl, 2-thienyl, 3, thienyl, 2-pyridyl, 3-pyridyl, 4-pyridyl, phenyl 3) an alkyl or alkenyl chain substituted with C5–C7 cycloalkyl.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence
<220> FEATURE:
```

```
<221> NAME/KEY: MOD_RES
<222> LOCATION: (1)..(1)
<223> OTHER INFORMATION: N-succinyl-alanine
<220> FEATURE:
<221> NAME/KEY: MOD_RES
<222> LOCATION: (4)..(4)
<223> OTHER INFORMATION: phenylalanine-para-nitroanilide

<400> SEQUENCE: 1

Ala Phe Pro Phe
1
```